(12) United States Patent
Lesko

(10) Patent No.: US 10,575,917 B2
(45) Date of Patent: Mar. 3, 2020

(54) ULTRASONIC SURGICAL INSTRUMENT WITH INTEGRAL TORQUE WRENCH AND TRANSVERSE ENGAGEMENT

(71) Applicant: ETHICON ENDO-SURGERY, LLC, Guaynabo, PR (US)

(72) Inventor: Jason R. Lesko, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 528 days.

(21) Appl. No.: 15/378,414

(22) Filed: Dec. 14, 2016

(65) Prior Publication Data

US 2018/0161058 A1 Jun. 14, 2018

(51) Int. Cl.
*A61B 18/18* (2006.01)
*A61B 90/00* (2016.01)
*A61N 7/02* (2006.01)
*A61B 17/32* (2006.01)
*A61B 18/00* (2006.01)
*A61B 17/00* (2006.01)

(52) U.S. Cl.
CPC ...... *A61B 90/03* (2016.02); *A61B 17/320068* (2013.01); *A61N 7/02* (2013.01); *A61B 2017/00477* (2013.01); *A61B 2017/320071* (2017.08); *A61B 2017/320094* (2017.08); *A61B 2017/320095* (2017.08); *A61B 2018/0063* (2013.01); *A61B 2018/00345* (2013.01); *A61B 2018/00601* (2013.01); *A61B 2018/00619* (2013.01); *A61B 2090/031* (2016.02)

(58) Field of Classification Search
CPC combination set(s) only.
See application file for complete search history.

(56) References Cited

U.S. PATENT DOCUMENTS

| 5,322,055 | A | 6/1994 | Davison et al. |
| 5,873,873 | A | 2/1999 | Smith et al. |
| 5,897,523 | A | 4/1999 | Wright et al. |
| 5,980,510 | A | 11/1999 | Tsonton et al. |

(Continued)

OTHER PUBLICATIONS

U.S. Appl. No. 61/410,603, filed Nov. 5, 2010.

(Continued)

*Primary Examiner* — Michael F Peffley
*Assistant Examiner* — Amanda L Zink
(74) *Attorney, Agent, or Firm* — Frost Brown Todd LLC

(57) ABSTRACT

A surgical instrument includes an instrument body, an ultrasonic transducer assembly, and a slip lock having a lock member configured to move between unlocked and locked positions and an arrester. The transducer assembly is rotatably mounted along a longitudinal axis within the body such that the transducer assembly is configured to selectively rotate. The arrester has a catch portion and a deflectable portion, which is configured to deflect relative to the transducer assembly. The catch portion is configured to seize the transducer assembly and selectively inhibit rotation for rotatably coupling with the acoustic waveguide up to a predetermined torque. The deflectable portion is configured to deflect relative to the transducer assembly upon receiving a torque greater than the predetermined torque. Accordingly, the catch portion releases the transducer assembly to slip relative to the catch portion for limiting coupling of the transducer assembly with the acoustic waveguide to the predetermined torque.

20 Claims, 13 Drawing Sheets

(56) References Cited

U.S. PATENT DOCUMENTS

| | | |
|---|---|---|
| 5,989,264 A | 11/1999 | Wright |
| 6,063,098 A | 5/2000 | Houser et al. |
| 6,090,120 A | 7/2000 | Wright |
| 6,325,811 B1 | 12/2001 | Messerly |
| 6,454,782 B1 | 9/2002 | Schwemberger |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 7,135,030 B2 | 11/2006 | Schwemberger et al. |
| 7,621,930 B2 | 11/2009 | Houser |
| 8,461,744 B2 | 6/2013 | Wiener et al. |
| 8,591,536 B2 | 11/2013 | Robertson |
| 8,623,027 B2 | 1/2014 | Price et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,402,682 B2 | 8/2016 | Worrell |
| 9,408,622 B2 | 8/2016 | Stulen et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2014/0107684 A1* | 4/2014 | Craig ............. A61B 17/320092 606/169 |
| 2015/0080924 A1 | 3/2015 | Stulen et al. |
| 2015/0245850 A1* | 9/2015 | Hibner ............... A61B 18/1482 606/171 |
| 2015/0265309 A1* | 9/2015 | Boudreaux .... A61B 17/320092 606/169 |
| 2016/0015419 A1 | 1/2016 | Hibner et al. |

OTHER PUBLICATIONS

U.S. Appl. No. 14/258,179, filed Apr. 22, 2014.
U.S. Appl. No. 15/378,432, filed Dec. 14, 2016.
U.S. Appl. No. 15/378,452, filed Dec. 14, 2016.
U.S. Appl. No. 15/378,391, filed Dec. 14, 2016.

* cited by examiner

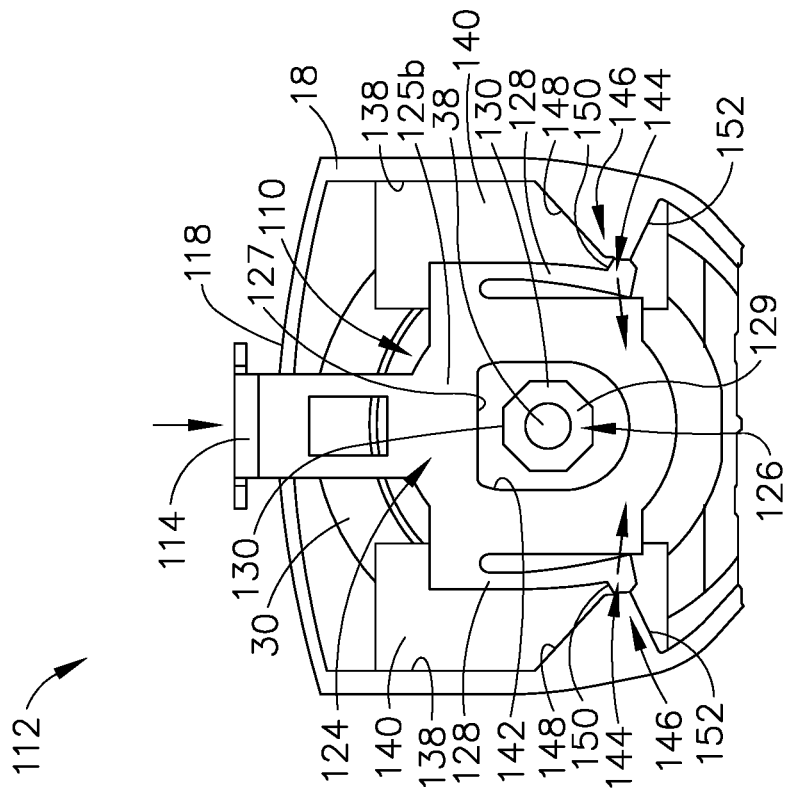
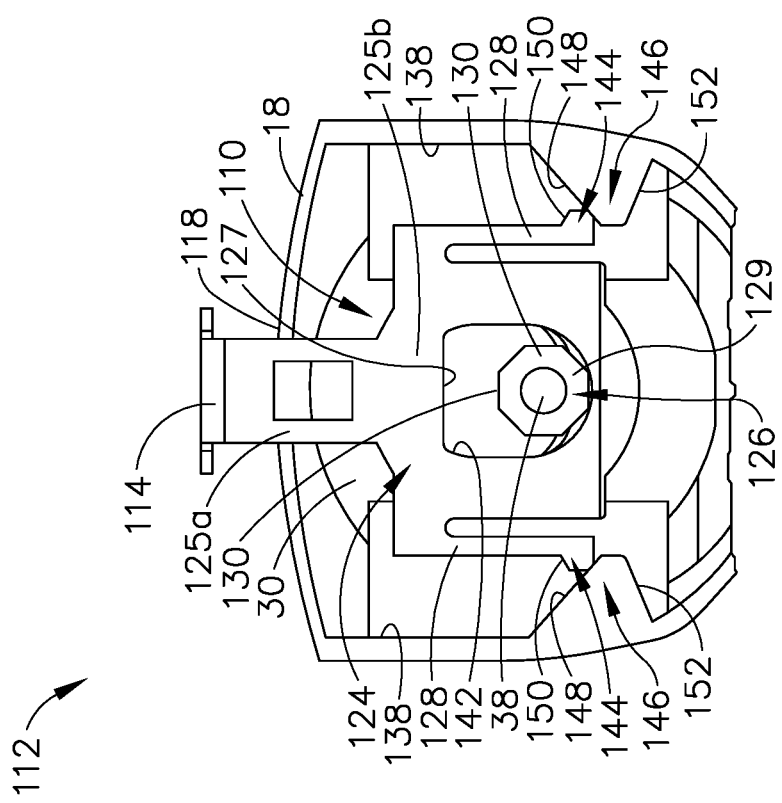

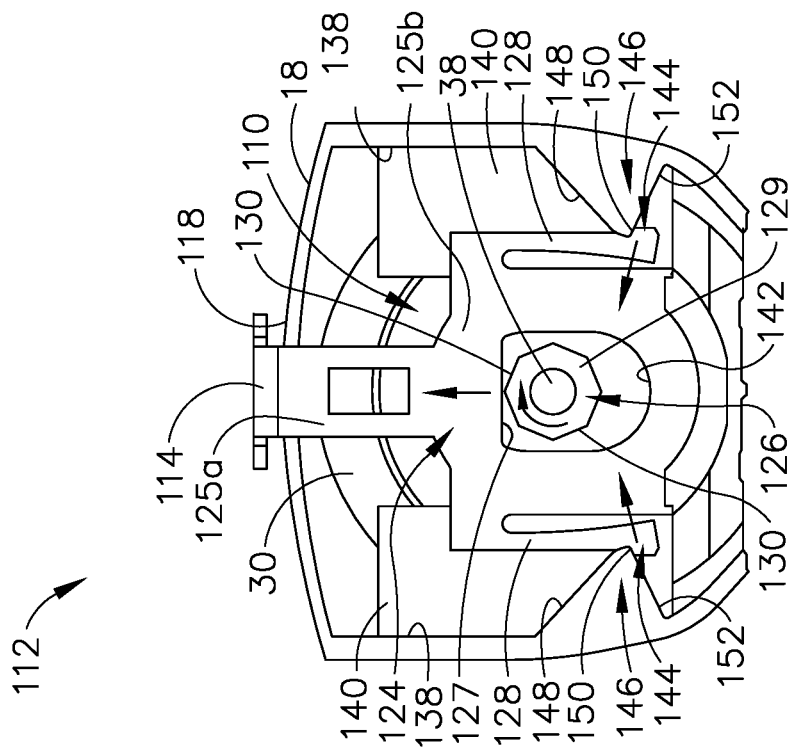

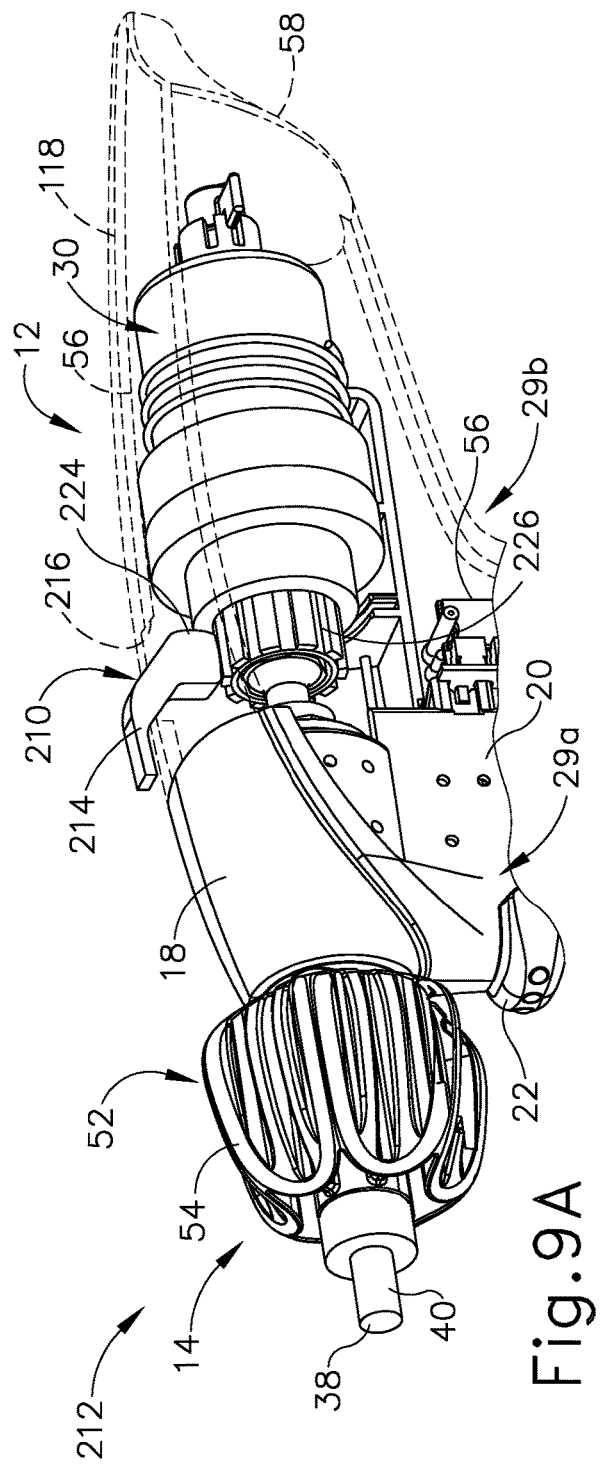
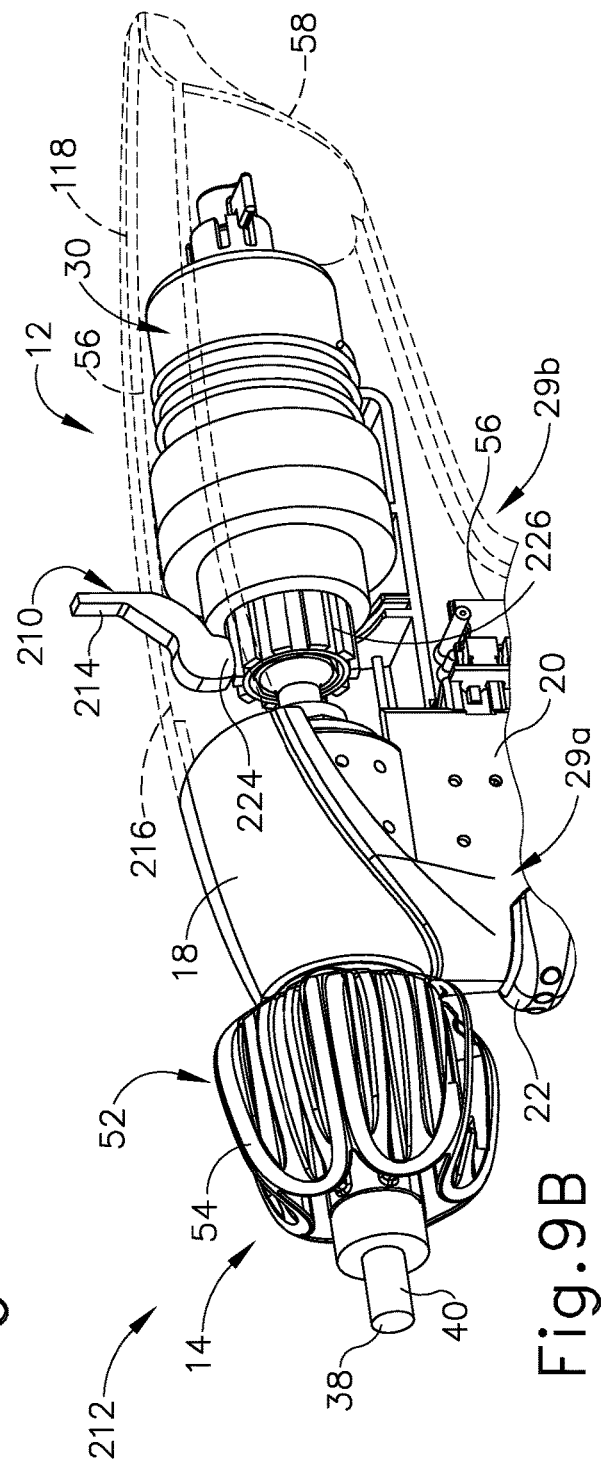

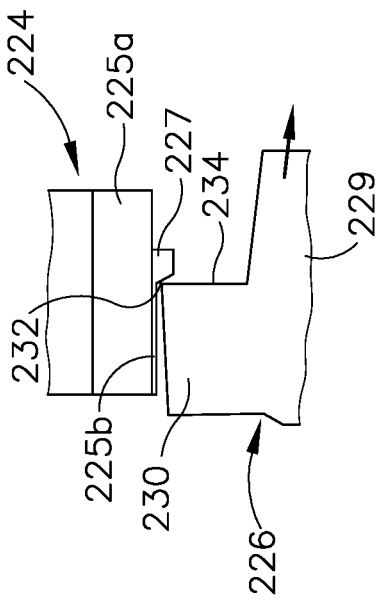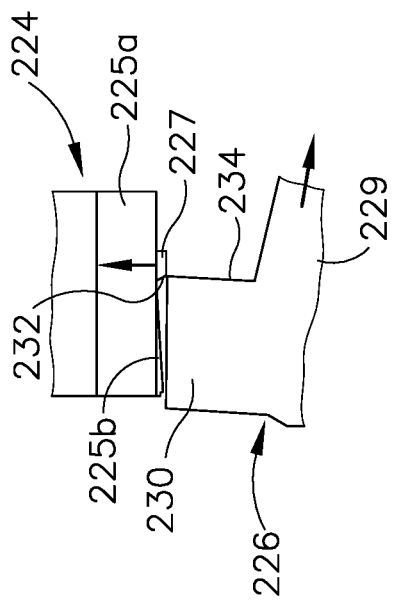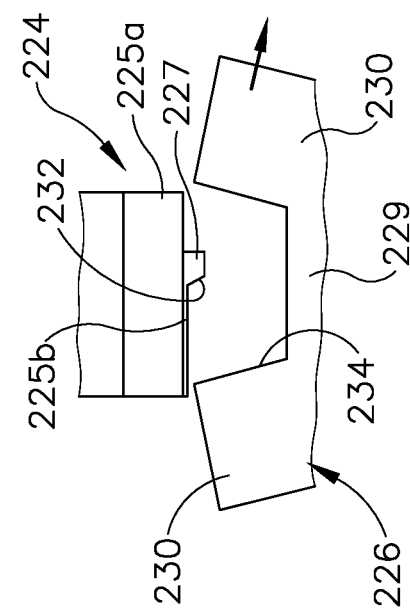

ULTRASONIC SURGICAL INSTRUMENT WITH INTEGRAL TORQUE WRENCH AND TRANSVERSE ENGAGEMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. patent application Ser. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9,2016, the disclosure of which is incorporated by reference herein; U.S. Pub. No. 2014/0114334, entitled "Flexible Harmonic Waveguides/Blades for Surgical instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, now U.S. Provisional App. No. 62/172,880, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8A depicts an enlarged cross-sectional end view of the handle assembly of FIG. 7A taken along section line 7A-7A of FIG. 5 to show the translational slip lock in the unlocked position;

FIG. 8B depicts an enlarged cross-sectional end view of the handle assembly of FIG. 7A taken along section line 7A-7A of FIG. 5 to show the translational slip lock being depressed from the unlocked position toward the locked position;

FIG. 8C depicts an enlarged cross-sectional end view of the handle assembly of FIG. 7A taken along section line 7A-7A of FIG. 5 to show the translational slip lock depressed to the locked position again to inhibit rotation of an ultrasonic transducer assembly of the ultrasonic surgical instrument of FIG. 5;

FIG. 8D depicts an enlarged cross-sectional end view of the handle assembly of FIG. 7A taken along section line 7A-7A of FIG. 5 to show the ultrasonic transducer assembly slipping relative to the translational slip lock to limit coupling torque between an acoustic waveguide and the ultrasonic transducer assembly of the ultrasonic surgical instrument of FIG. 5;

FIG. 9A depicts an enlarged perspective view of a third exemplary ultrasonic surgical instrument with a pivot slip lock having various components removed for more clearly showing the ultrasonic transducer assembly and the pivot slip lock in an unlocked position;

FIG. 9B depicts an enlarged perspective view of a third exemplary ultrasonic surgical instrument with a pivot slip lock having various components removed for more clearly showing the pivot slip lock in a locked position;

FIG. 14A depicts an enlarged cross-sectional view of the pivot slip lock in the locked position as shown in FIG. 11B;

FIG. 14B depicts an enlarged cross-sectional view of the pivot slip lock in the locked position as shown in FIG. 11B, with the arrester of FIG. 12 inhibiting rotation of the engagement collar of FIG. 13; and FIG. 14C depicts an enlarged cross-sectional view of the pivot slip lock in the locked position as shown in FIG. 11B, with a portion of the arrester deflecting to limit coupling torque between an acoustic waveguide an ultrasonic transducer of the ultrasonic transducer assembly of FIG. 9A.

Figure 1:
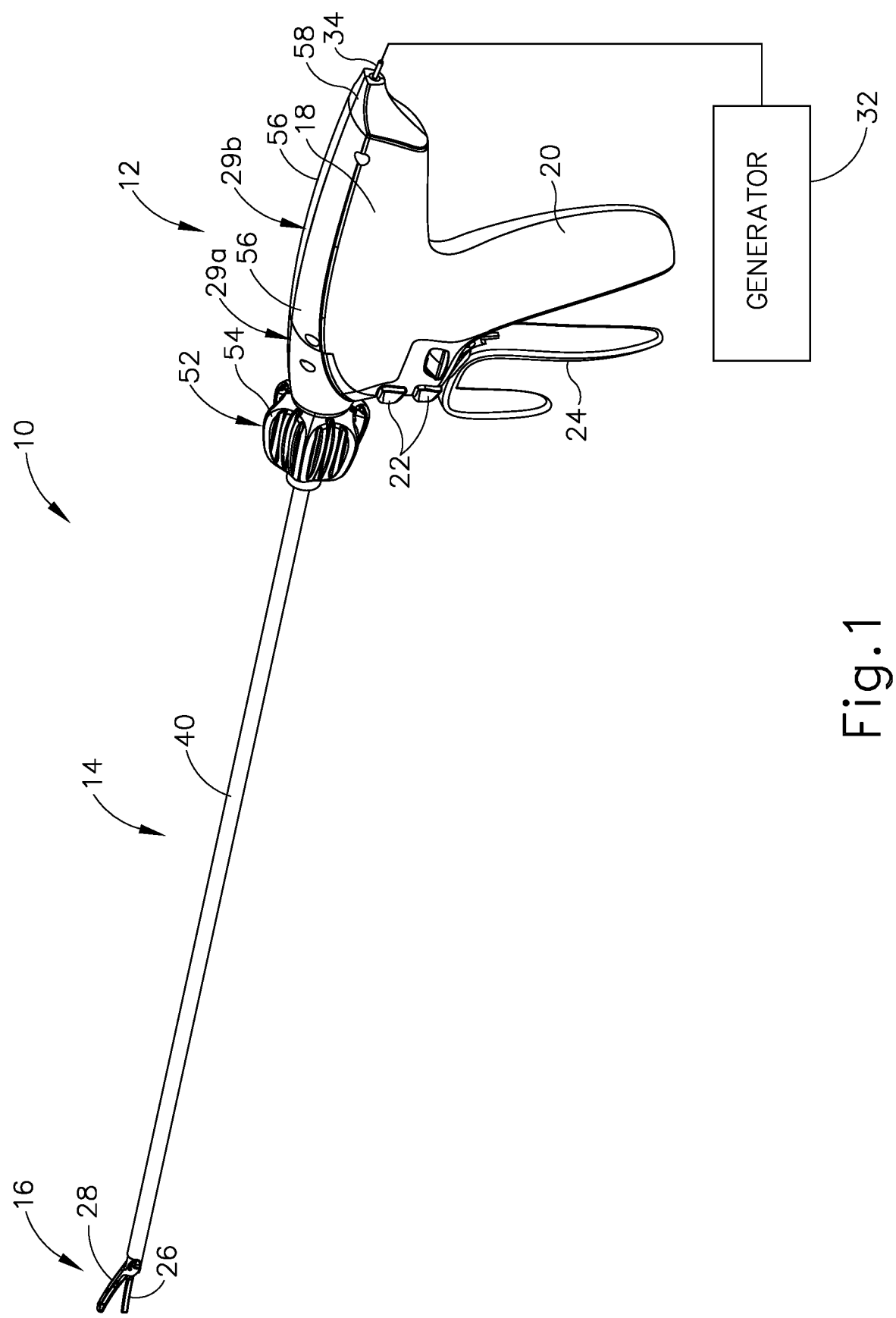
FIG. 1 depicts a perspective view of a first exemplary ultrasonic surgical instrument having a handle assembly, a shaft assembly, and an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "upper," "lower," "inner," and "outer" are used herein with respect to the drawings, However, surgical instruments are used in many orientations and positions, and these terms are not intended to be limiting and absolute. The terms "proximal," "distal," "upper," "lower," "inner," and "outer" are thus relative terms and not intended to unnecessarily limit the invention described herein.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (12), a shaft assembly (14), and an end effector (16). Handle assembly (12) comprises a body (18) including a pistol grip (20) and a pair of buttons (22). Handle assembly (12) also includes a trigger (24) that is pivotable toward and away from pistol grip (20). It should be understood, however, that various other suitable configurations may be used, including but not limited to a scissor grip configuration. End effector (16) includes an ultrasonic blade (26) and a pivoting clamp arm (28). Clamp arm (28) is coupled with trigger (24) such that clamp arm (28) is pivotable toward ultrasonic blade (26) in response to pivoting of trigger (24) toward pistol grip (20); and such that clamp arm (28) is pivotable away from ultrasonic blade (26) in response to pivoting of trigger (24) away from pistol grip (20). Various suitable ways in which clamp arm (28) may be coupled with trigger (24) will be apparent to those of ordinary skill in the art in view of the teachings herein. In some versions, one or more resilient members are used to bias clamp arm (28) and/or trigger (24) to the open position shown in FIG. 1.

Figure 2:
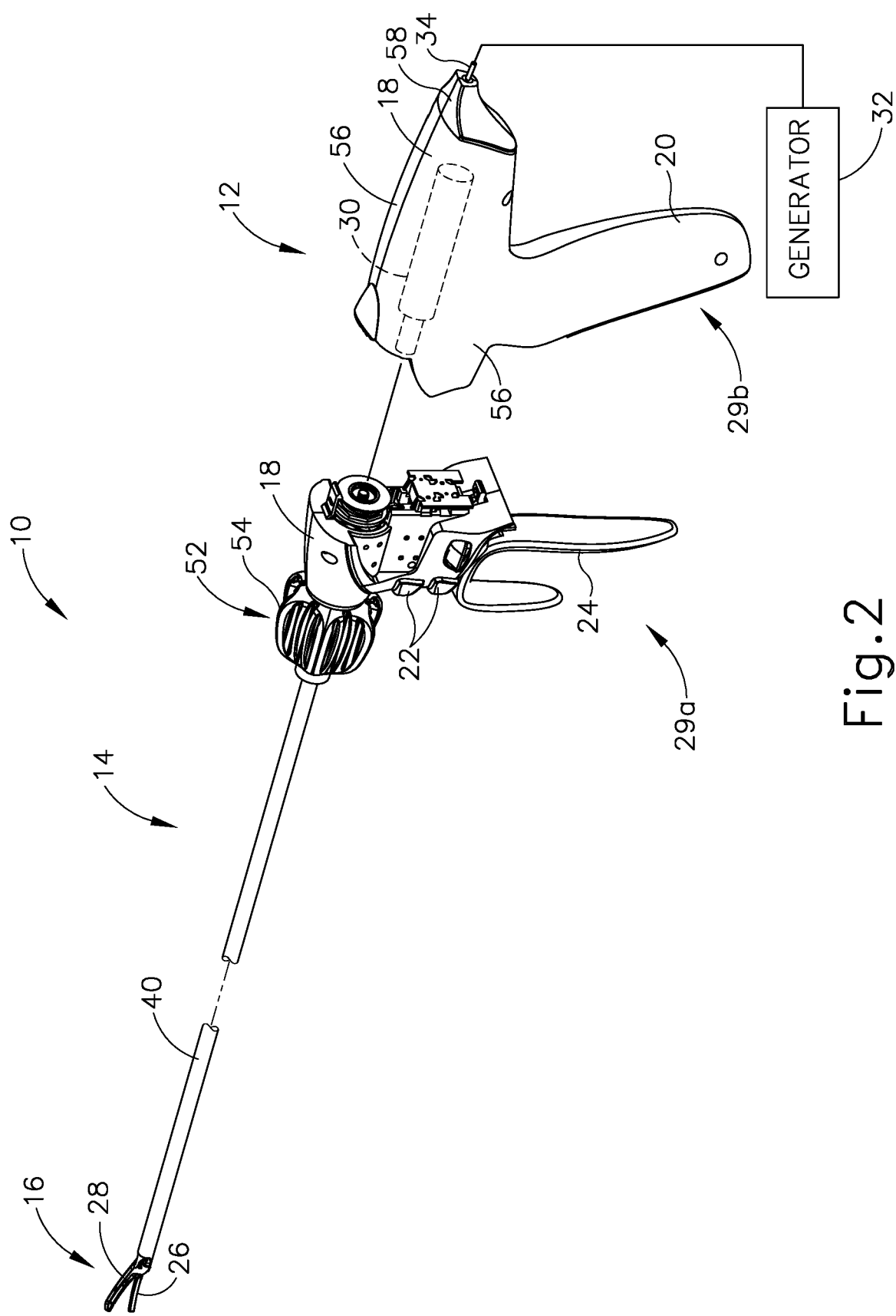
FIG. 2 depicts a partially exploded view the ultrasonic surgical instrument of FIG. 1 with a disposable portion of the ultrasonic surgical instrument removed from a reusable portion of the ultrasonic surgical instrument.

Furthermore, instrument (10) of this example comprises a disposable assembly (29a) and a reusable assembly (29b) as illustrated in FIG. 2 in more detail. By way of example, disposable assembly (29a) generally includes shaft assembly (14), end effector (16), buttons (22), trigger (24), and a portion of body (18). By way of further example, reusable assembly (29b) generally includes the remaining portion of body (18) with pistol grip (20) and an ultrasonic transducer assembly (30) (see FIG. 5). The distal portion of reusable assembly (29b) is configured to removably receive the proximal portion of disposable assembly (29a), as seen in FIGS. 1-2, to form instrument (10). To accommodate such disposable and reusable assemblies (29a, 29b), shaft assembly (14) and ultrasonic transducer assembly (30) (see FIG. 5) are configured to removably couple together as will be discussed below in greater detail.

Ultrasonic transducer assembly (30) is positioned within body (18) of handle assembly (12). Transducer assembly (30) is coupled with a generator (32) via a cable (34), such that transducer assembly (30) receives electrical power from generator (32) via cable (34). Piezoelectric elements in transducer assembly (30) convert electrical power from generator (32) into ultrasonic vibrations. Generator (32) ay include a power source and control module that is configured to provide a power profile to transducer assembly (30) that is particularly suited for the generation of ultrasonic vibrations through transducer assembly (30). By way of example only, generator (32) may comprise a GEN04 or GEN11 sold by Ethicon Endo-Surgery, Inc. of Cincinnati, Ohio. In addition, or in the alternative, generator (32) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (32) may be integrated into handle assembly (12), and that handle assembly (12) may even include a battery or other on-board power source such that cable (34) is omitted, while other cables may alternatively be used for electrically coupling various components. Still other suitable forms that generator (32) may take, as well as various features and operabilities that generator (32) may provide, will be apparent to those of ordinary skill in the art in view of the teachings herein.

In an exemplary use, assemblies (29a, 29b) are coupled together to form instalment (10) and then is used to perform the surgical procedure. Assemblies (29a, 29b) are then decoupled from each other for further processing. In some instances, after the surgical procedure is complete, disposable assembly (29a) is immediately disposed of while reusable assembly (29b) is sterilized and otherwise processed for re-use. By way of example only, reusable assembly (29b) may be sterilized in a conventional relatively low temperature, relatively low pressure, hydrogen peroxide sterilization process. Alternatively, reusable assembly (29b) may be sterilized using any other suitable systems and techniques. In some versions, reusable assembly (29b) may be sterilized and reused approximately 100 times. Alternatively, reusable assembly (29b) may be subject to any other suitable life cycle. For instance, reusable assembly (29b) may be disposed of after a single use, if desired. While disposable assembly (29a) is referred to herein as being "disposable," it should be understood that, in some instances, disposable assembly (29a) may also be sterilized and otherwise processed for re-use. By way of example only, disposable assembly (29a) may be sterilized and reused approximately 2-30 times, using any suitable systems and techniques. Alternatively, disposable assembly (29a) may be subject to any other suitable life cycle.

In some versions, disposable assembly (29a) and/or reusable assembly (29b) includes one or more features that are operable to track usage of the corresponding assembly (29a, 29b), and selectively restrict operability of the corresponding assembly (29a, 29b) based on use. For instance, disposable assembly (29a) and/or reusable assembly (29b) may include one or more counting sensors and a control logic (e.g., microprocessor, etc.) that is in communication with the counting sensor(s). The counting sensor(s) may be able to detect the number of times instrument (10) is activated, the number of surgical procedures the corresponding assembly (29a, 29b) is used in, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (29a, 29b). In instances where the control logic stores two or more threshold values (e.g., a first threshold for number of activations and a second threshold for number of surgical procedures, etc.), the control logic may disable operability of one or more components in the corresponding assembly (29a, 29b) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10). Additional and/or alternative features with respect to alternative disposable and reusable assemblies (29a, 29b) may be constructed in accordance with at least some of the teachings of U.S. Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein. In any case the invention described herein is not intended to be limited to use with only replaceable or reusable components as described herein.

A. Exemplary End Effector and Shaft Assembly

Figure 3A:
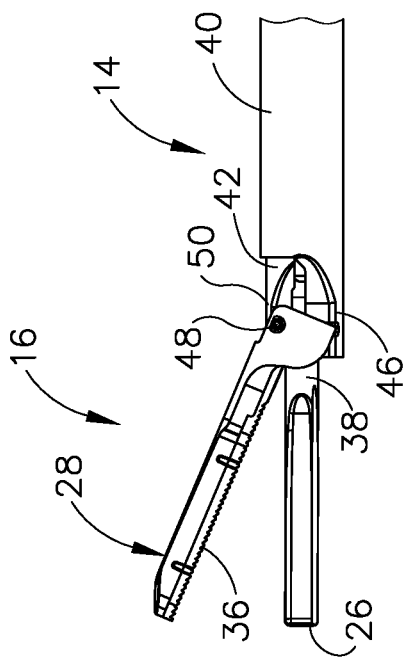
FIG. 3A depicts an enlarged side elevational view of the end effector of FIG. 1 in a closed position.
Figure 3B:
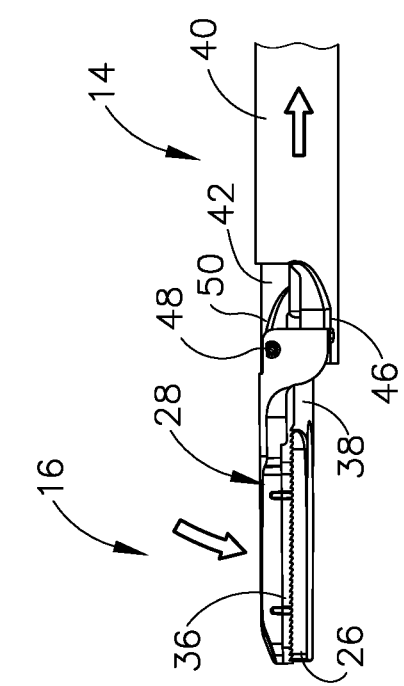
FIG. 3B depicts an enlarged side elevational view of the end effector of FIG. 1 in an open position.

As best seen in FIGS. 3A-3B, end effector (16) of this example comprises clamp arm (28) and ultrasonic blade (26) as discussed briefly above. Clamp arm (28) includes a clamp pad (36), which faces blade (26). Clamp arm (28) is pivotable toward and away from blade (26) to selectively compress tissue between clamp pad (36) and blade (26). More particularly, blade (26) is an integral feature of a distal end of an acoustic waveguide (38), which extends coaxially through tubes (40, 42), and which is configured to communicate ultrasonic vibrations to blade (26) as will be described in greater detail below.

Shaft assembly (14) comprises an outer tube (40) and an inner tube (42). Outer tube (40) is operable to translate longitudinally relative to inner tube (42) to selectively pivot clamp arm (28) toward and away from blade (26). To accomplish this, integral pin features (not shown) extending inwardly from respective projections (44) of clamp arm (28) pivotally secure a first portion of clamp arm (28) to a distally projecting tongue (46) of outer tube (40); while an inserted pin (48) pivotally secures a second portion of clamp arm (28) to a distally projecting tongue (50) of inner tube (42). Thus, tubes (40, 42) cooperate to pivot clamp arm (28) toward blade (26) when outer tube (40) is retracted proximally relative to inner tube (42). It should be understood that clamp arm (28) may be pivoted back away from blade (26) by translating outer tube (40) distally relative to inner tube (42). In an exemplary use, clamp arm (28) may be pivoted toward blade (26) to grasp, compress, seal, and sever tissue captured between clamp pad (36) and blade (26) as shown in FIG. 3A. Clamp arm (28) may also be pivoted away from blade (26), as shown in FIG. 3B, to release tissue from between clamp pad (36) and blade (26); and/or to perform blunt dissection of tissue engaging opposing outer surfaces of clamp arm (28) and blade (26). In some alternative versions, inner tube (42) translates while outer tube (40) remains stationary to provide pivotal movement of clamp arm (28).

As shown in FIGS. 1-2, shaft assembly (14) of the present example extends distally from handle assembly (12). A rotation control assembly (52) has a rotation control member in the form of rotation control knob (54), which is secured to a proximal portion of outer tube (40). Knob (54) is rotatable relative to body (18), such that shaft assembly (14) is rotatable about the longitudinal axis defined by outer tube (40), relative to handle assembly (12). Such rotation may provide rotation of end effector (16) and shaft assembly (30) unitarily, which also includes unitary rotation of acoustic waveguide (38) coupled with transducer assembly (30) within handle assembly (12). In some other versions, various rotatable features may simply be omitted and/or replaced with alternative rotatable features, if desired.

While the present shaft assembly (14) is generally rigid and linear, it will be appreciated that alternative shaft assemblies may include an articulation section (not shown) for deflecting end effector (16) at various lateral deflection angles relative to a longitudinal axis defined by outer tube (40). It will be appreciated that such an articulation section may take a variety of forms. By way of example only, such an articulation section may be configured in accordance with one or more teachings of U.S. Pub. No. 2012/0078247, entitled "Articulation Joint Features for Articulation Surgical Device," published on Mar. 29, 2012, issued as U.S. Pat. No. 9,402,682 on Aug. 2, 2016, the disclosure of which is incorporated by reference herein. As another merely illustrative example, an articulation section may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. Various other suitable forms that an articulation section may take will be apparent to those of ordinary skill in the art in view of the teachings herein.

B. Exemplary Handle Assembly

As seen in FIGS. 1 and 2, handle assembly (12) is reusable as discussed above and comprises body (18) defined by a pair of complementary housings (56) joined together. Housings (56) collectively define pistol grip (20) and include a cord support base (58) through which cable (34) extends between transducer assembly (30) and generator (32). While body (18) includes pistol grip (20) in this example, it should be understood that any other suitable kind of grip may be used.

Waveguide (38) extends proximally through knob (54) and into body (18) to mechanically couple with transducer assembly (30). When waveguide (38) is sufficiently coupled with transducer assembly (30), ultrasonic vibrations that are generated by transducer assembly (30) are communicated along waveguide (38) to reach blade (26). In the present example, the distal end of blade (26) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (30) is energized, the distal end of blade (26) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz, When transducer assembly (30) of the present example is activated, these mechanical oscillations are transmitted through waveguide (38) to reach blade (26), thereby providing oscillation of blade (26) at the resonant ultrasonic frequency. Thus, when tissue is secured between blade (26) and clamp pad (36), the ultrasonic oscillation of blade (26) may simultaneously sever the tissue and denature the proteins in adjacent tissue cells, thereby providing a coagulative effect with relatively little thermal spread. In sonic versions, an electrical current may also be provided through blade (26) and/or clamp pad (36) to also seal the tissue.

Further exemplary features and operabilities for disposable and/or reusable portions of surgical instrument (10) will be described in greater detail below, while other variations will be apparent to those of ordinary skill in the art in view of the teachings.

C. Exemplary Torque Wrench

Figure 4:
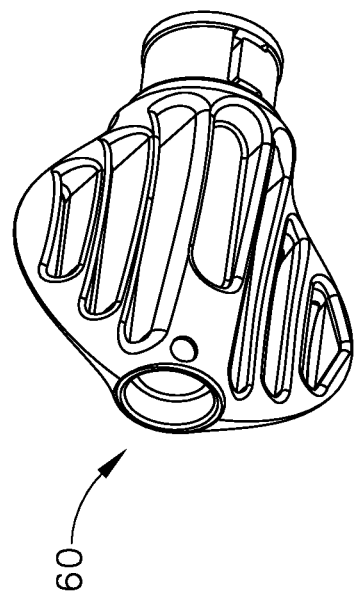
FIG. 4 depicts a perspective view of a torque wrench for coupling the shaft assembly of FIG. 1 to the handle assembly of FIG. 1.

In the present example, waveguide (38) is threadably secured to transducer assembly (30) for acoustically coupling waveguide (38) with transducer assembly (30) for use. In order to properly communicate the resonant ultrasonic vibrations from transducer assembly (30) to waveguide (38), a predetermined torque is applied to waveguide (38) during installation with transducer assembly (30). As seen in FIG. 4, a separate torque wrench (60) is used to couple the waveguide (38) with the transducer assembly (30) to inhibit overtightening of the waveguide (38). It should be understood that torque wrench (60) may ensure that a sufficient level of torque is used to couple waveguide (38) with transducer assembly (30) (i.e., to avoid separation of waveguide (38) from transducer assembly (30) while waveguide (38) and transducer assembly (30) are ultrasonically activated); while also preventing too much torque from being used to couple waveguide (38) with transducer assembly (30) (i.e., to avoid undue stress and the risk of breakage at the coupling of waveguide (38) from transducer assembly (30) while waveguide (38) and transducer assembly (30) are ultrasonically activated).

Torque wrench (60) of the present example may be slid proximally along shaft assembly (14) until torque wrench (60) engages knob (54), such that rotating torque wrench (60) similarly rotates knob (54), thereby rotating shaft assembly (14). During installation, a proximal end portion of waveguide (38) is received within a threaded hole (not shown) of transducer assembly (30). The operator rotates shaft assembly (14) via torque wrench (60), while holding handle assembly (12) stationary, thereby rotating waveguide (38) relative to transducer assembly (30). The proximal end portion of waveguide (38) is thus rotated into threaded engagement with transducer assembly (30). As installation torque increases during rotation, torque wrench (60) is configured to slip relative to knob (54) once the applied torque being transmitted therethrough exceeds the predetermined torque. In addition to slipping, torque wrench (60) generates audible and tactile "clicks" once the predetermined torque is achieved. Torque wrench (60) thus inhibits overtightening of waveguide (38) to transducer assembly (30). By way of further example only, torque wrench (60) may be configured and operable in accordance with at least some of the teachings of U.S. Pub. No. 2007/0191713, entitled "Ultrasonic Device for Cutting and Coagulating," published Aug. 16, 2007, now abandoned, the disclosure of which is incorporated by reference herein.

II. Handle Assembly with Integral Torque Wrench for Coupling Waveguide with Transducer Assembly As described above with respect to surgical instrument (10), once waveguide (38) and transducer assembly (30) are secured together at the predetermined torque, selective rotation of knob (54) collectively rotates the remainder of shaft assembly (14), end effector (16), waveguide (38), and transducer assembly (30) relative to handle assembly (12). However, even before proper installation at the predetermined torque, the proximal end of waveguide (38) may have enough frictional engagement with transducer assembly (30) to cause transducer assembly (30) to rotate with waveguide (38) relative to handle assembly (12). Such engagement may make it difficult, or even impossible in some cases, for a user to apply the predetermined torque for proper coupling of the waveguide (38) to transducer assembly (30), because the user may not be able to apply a reactionary torque to transducer assembly (30) up to the predetermined torque.

In order to facilitate coupling of waveguide (38) with transducer assembly (30), some versions of surgical instrument (10) may include a transducer lock. Various exemplary transducer locks are described in greater detail in U.S. patent application Ser. No. 15/378,432, entitled "Ultrasonic Surgical Instrument with Integral Shaft Assembly Torque Wrench," filed on Dec. 14, 2016, published as U.S. Pub. No. 2018/0161059 on June 14, 2018, the disclosure of which is incorporated by reference herein; U.S. patent application Ser. No. 15/378,452, entitled "Ultrasonic Surgical Instrument with Transducer Locking Feature," tiled on Dec. 14, 2016, published as U.S. Pub. No. 2018/0161060 on Jun. 14, 2018, the disclosure of which is incorporated by reference herein; and U.S. patent application Ser. No. 15/378,391, entitled "Ultrasonic Surgical Instrument with Integral Torque Wrench and Longitudinal Engagement," filed on Dec. 14, 2016, published as U.S. Pub. No. 2018/0161057 on Jun. 14, 2018, the disclosure of which is incorporated by reference herein.

While a transducer lock may inhibit rotation of transducer assembly (30), the separate torque wrench (60) is applied to shaft assembly (14) in at least some of the above referenced examples for providing the predetermined torque while inhibiting overtightening of waveguide (38) with transducer assembly (30). However, handling and manipulating torque wrench (60) separately from surgical instrument (10) may add further complexity to the surgical procedure and may be difficult to manage in some instances. Moreover, torque wrench (60) may wear out over a number of uses and maintaining the torque wrench (not shown) to provide clear and accurate limitations on torque to the predetermined torque may also be difficult over time. It may thus be desirable to integrate a torque wrench (110, 210), or at least some of the features and operability of torque wrench (110, 210), into handle assembly (12) of surgical instrument (10) in order to provide both torque limiting and transducer assembly seizing features.

The following description relates to various exemplary torque wrenches (110, 210) integrated into surgical instruments (112, 212) discussed below in greater detail. Accordingly, like numbers described herein indicate like features with respect to each exemplary torque wrench (110, 210). While torque wrenches (110, 210) are configured to selectively inhibit, and even prevent, rotation of transducer assembly (30) relative to body (18), in addition to limiting torque, it will be appreciated that some rotation in alternative examples is possible in accordance with the invention. For example, alternative torque wrenches may not strictly prevent rotation, but at least inhibit rotation enough to provide a reactionary torque equal to at least the predetermined torque for proper installation. The invention is thus not intended to be unnecessarily limited to preventing all relative rotation between transducer assembly (30) and body (18).

A. Exemplary Integral Translational Slip Lock

Figure 5:
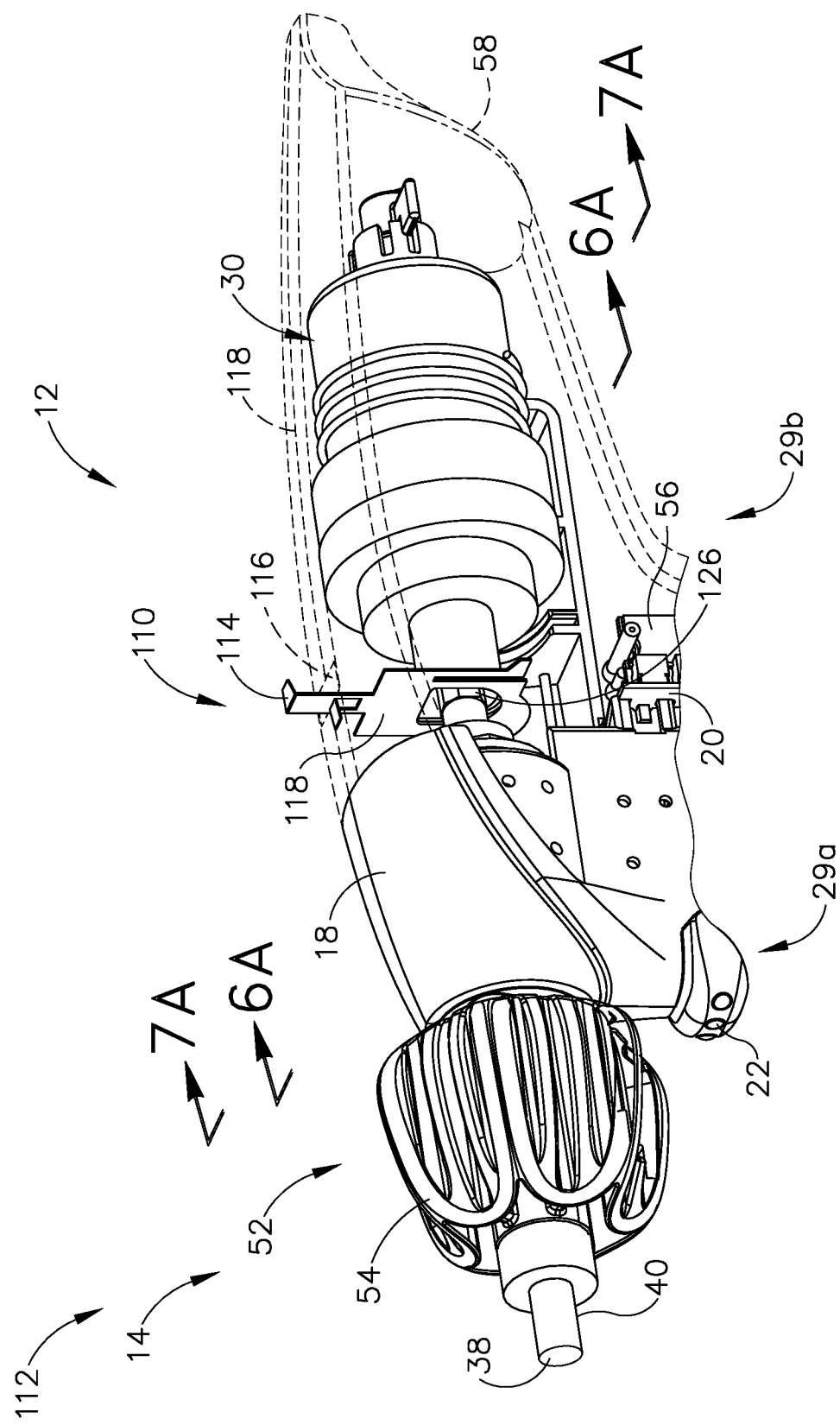
FIG. 5 depicts an enlarged perspective view of a second exemplary ultrasonic surgical instrument with a translational slip lock having various components removed for more clearly showing the ultrasonic transducer assembly and the translational slip lock in the unlocked position.
Figure 6A:
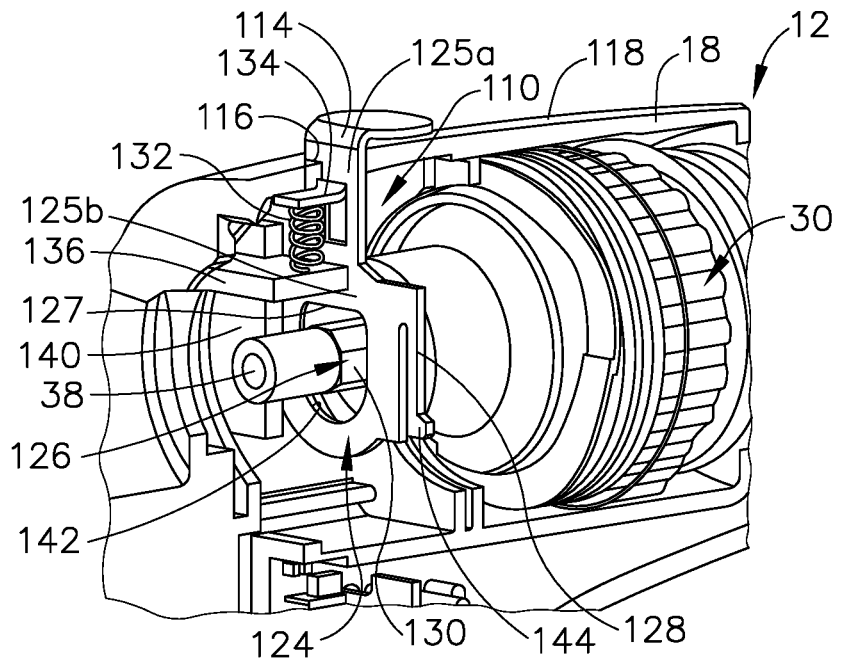
FIG. 6A depicts a perspective sectional view of a handle assembly of the ultrasonic surgical instrument of FIG. 5 taken along section line 6A-6A of FIG. 5 to show the translational slip lock in the unlocked position.
Figure 6B:
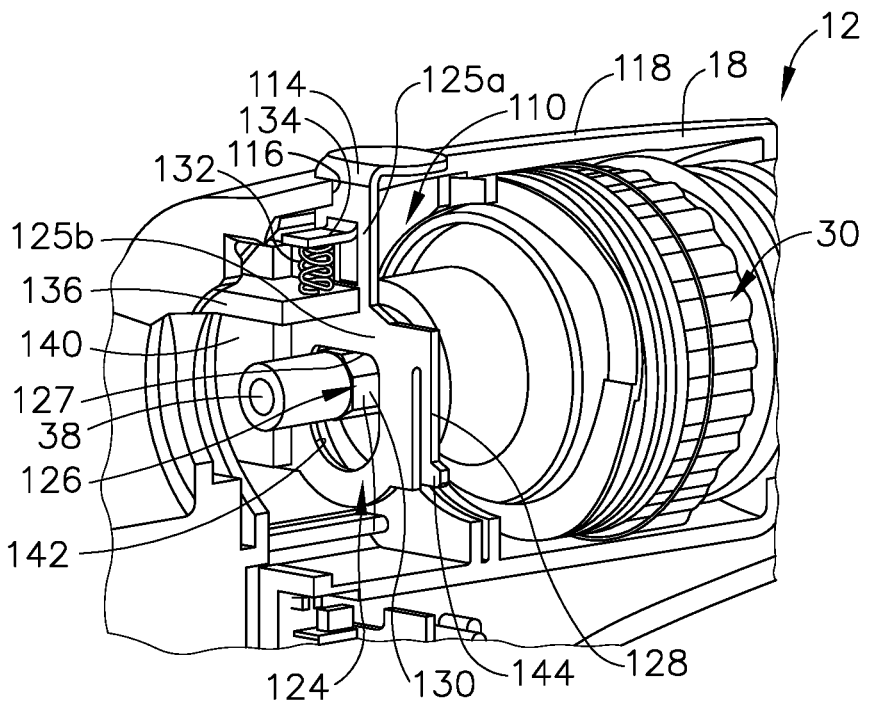
FIG. 6B depicts a perspective sectional view of a handle assembly of the ultrasonic surgical instrument of FIG. 5 taken along section line 6A-6A of FIG. 5 to show the translational slip lock in the locked position.
Figure 7A:
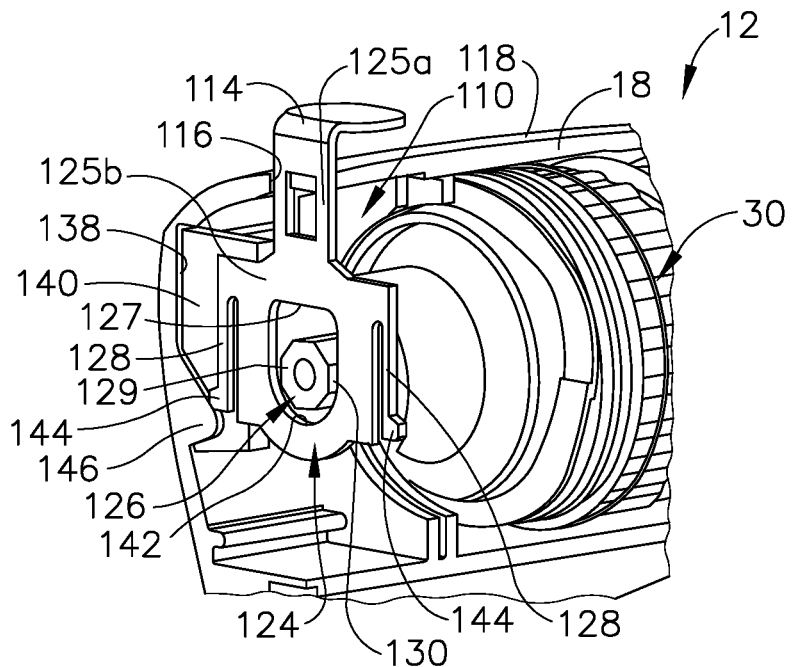
FIG. 7A depicts a perspective sectional view of a handle assembly of the ultrasonic surgical instrument of FIG. 5 taken along section line 7A-7A of FIG. 5 to show the translational slip lock in the unlocked position.
Figure 7B:
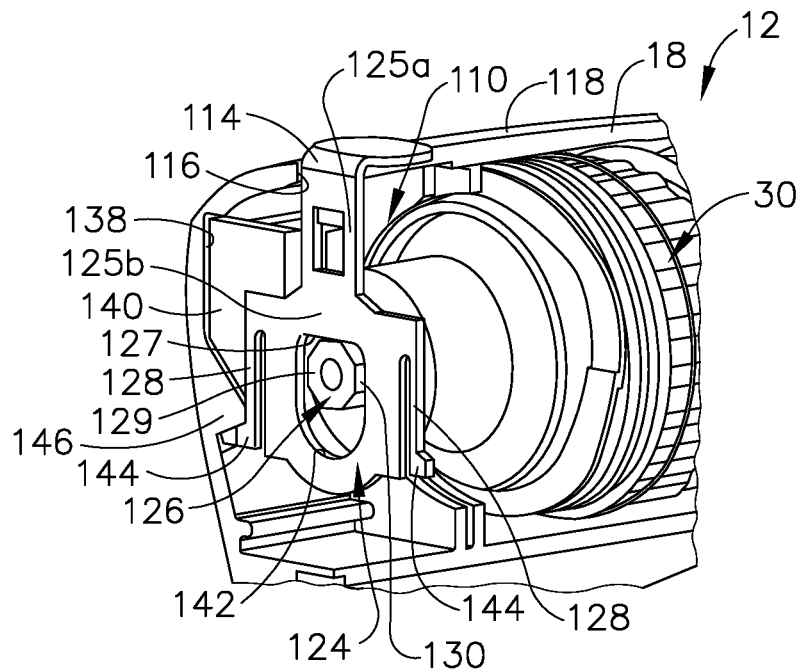
FIG. 7B depicts a perspective sectional view of a handle assembly of the ultrasonic surgical instrument of FIG. 5 taken along section line 7A-7A of FIG. 5 to show the translational slip lock in the locked position.

FIGS. 5-8D illustrate first exemplary torque wrench (110), such as an integral slip lock (110) of a surgical instrument (112), which is configured to both inhibit rotation of transducer assembly (30) relative to body (18) and limit torque applied to waveguide (38) to the predetermined torque. As shown in FIGS. 5-6B, slip lock (110) includes a lock switch (114) extending through a lock channel (116) in body (18). More particularly, lock channel (116) extends transversely through an upper surface (118) of body (18) directly above the longitudinal axis. Lock switch (114) is thus translatable between an upper, unlocked position and a lower, locked position for respectively unlocking and locking rotation of transducer assembly (30) relative to body (18). While lock switch (114) and lock channel (116) are positioned on upper surface (118) of body (18) in the present example, it will be appreciated that lock switch (114) and lock channel (116) may be alternatively positioned to cooperate with transducer assembly (30). The invention is thus not intended to be unnecessarily limited to having lock switch (114) and lock channel (116) positioned as shown herein.

While not shown with respect to the present example of slip lock (110), it will be appreciated that upper surface (118), or another portion of surgical instrument (112) may further include an "unlocked" indicia (not shown) and/or a "locked" indicia (not shown) for visually indicating a rotational state (i.e., unlocked state or locked state) of transducer assembly (30) to the user. Examples of unlocked and locked indicia are shown below in more detail with respect to FIGS. 10A-10B. However, it will be appreciated that alternative examples of unlocked and locked indicia may be used with surgical instrument (110) to indicate the rotational state of transducer assembly (30) to the user.

As seen in FIGS. 6A-7B, slip lock (110) further includes an arrester (124) operatively connected to lock switch (114) and an engagement feature (126) operatively connected to transducer assembly (30). Arrester (124) and engagement feature (126) are configured to cooperate with each other to selectively allow or inhibit rotation of transducer assembly (30) relative to body (18). Arrester (124) of the present example extends transversely downwardly from lock switch (114) toward the longitudinal axis and, in the unlocked position, is distally offset from engagement feature (126) and transducer assembly (30). More particularly, arrester (124) includes a downward stem (125a) extending transversely downwardly from lock switch (114) to an arrester body (125b), which also extends transversely downwardly from stem (125a).

Arrester body (125b) of the present example has a catch portion and a deflectable portion. Catch portion includes a catch surface (127) that is configured to transversely engage engagement feature for seizing transducer assembly (30). Deflectable portion includes a pair of resilient detent arms (128) configured to engage a portion of instrument body (18) to releasably secure catch surface (127) against engagement feature (126). As will be described below in greater detail, detent arms (128) are configured to deflect relative to catch surface (127) and engagement feature (127) upon application of torque to transducer assembly (30) greater than the predetermined torque upon installation of waveguide (38). In addition, while also limiting torque applied between waveguide (38) and transducer assembly (30), detent arms (128) also secure catch surface (127) and lock switch (114) in the locked position despite being biased toward the unlocked position as shown particularly in FIGS. 6A-6B. The user may then manipulate other portions of surgical instrument (112) without necessarily holding lock switch (114) in the locked position.

Engagement feature (126) of the present example is more particularly in the form of an engagement collar (126) having an annular collar body (129) and a plurality of flats (130) positioned angularly about annular collar body (129). Each flat (130) faces radially outwardly from annular collar body (129) such that any one flat (130) is configured to receive catch surface (127) of arrester (124) thereagainst. Furthermore, engagement collar (126) is rigidly secured to a distal end portion of transducer assembly (30) and positioned concentrically about the longitudinal axis. Engagement collar (126) is thus rotatably fixed relative to transducer assembly (30) such that each may either rotate together relative to body (18) or be rotatably secured together relative to body (18). The present example of annular collar body (129) includes six flats (130) equiangularly positioned about the longitudinal axis to define a hexagonal shape. Each flat (130) extends in the longitudinal direction to be parallel with the longitudinal axis; and, when rotated to the uppermost position about the longitudinal axis, is parallel with catch surface (127) of arrester (124), which in the present example includes a catch flat (127). Thus, regardless of the rotatable position of transducer assembly (39) at least one flat (130) is positioned to receive catch flat (127) of arrester (124) thereagainst for engagement. However, it will be appreciated that alternative numbers of flats (127, 130) or even alternative structures may be cooperatively used with other surfaces to releasably secure catch surface (127) against engagement collar (126) for inhibiting rotation of transducer assembly (30).

FIGS. 6A-7B further illustrate arrester (124) translatably mounted within body (18) and configured to move from an upper, disengaged position to a lower, engaged position. As briefly discussed above, arrester (124) is biased upwardly toward the disengaged position by a spring (132) captured in body (18) and arrester (124). More particularly, transverse stem (125a) includes a tab mount (134) projecting distally above a body mount (136), which laterally extends within body (18). Spring (132) is captured in compression between tab and body mounts (134, 236) such that spring (132) urges tab mount (134) upwardly, thereby directing arrester (124) toward the disengaged position and lock switch (114) toward the locked position. While arrester (124) may be translated up and down between disengaged and engaged positions via manipulation of lock switch (114) by the user, arrester (124) is secured longitudinally within a mount slot (138) defined between a pair of mount plates (140) as seen with respect to FIG. 6A and FIG. 7A. Each lateral side of body (18) has one pair of inwardly extending mount plates (140) with mount slot (138) positioned therebetween to receive opposing lateral portions of arrester (124). Of course, it will be appreciated that alternative structures configured to longitudinally fix arrester (124) within body (18) may be similarly used. Accordingly, the invention is not intended to be unnecessarily limited to the particular mount plates (140) and mount slot (138) described herein.

In the disengaged position shown in FIG. 6A, engagement collar (126) is received within a longitudinally extending arrester hole (142) at least partially defined in the present example by catch surface (127). Catch surface (127) in the disengaged position thus remains offset from engagement collar (126) to allow engagement collar (126) and transducer assembly (30) to freely rotate together. However, translating catch surface (127) against one of flats (130) of engagement collar (126) tends to inhibit relative rotation as shown in FIG. 6B. Moreover, releasably securing catch surface (127) against one of flats (127) with a predetermined compression force tuned to the predetermined torque inhibits relative rotation up to the predetermined torque, but then effectively releases engagement collar (126) to allow for relative slippage between engagement collar (126) and catch surface (127). In the present example, deflection of detent arms (128) balanced with the upward biasing force of spring (132) are collectively configured to apply this predetermined compression force in the engaged position.

To this end, FIGS. 7A-8B illustrate detent arms (128) respectively positioned within mount slots (138) and configured to releasably secure catch surface (127) against engagement collar (126) with the predetermined compression force. Each detent arm (128) extends transversely from arrester body (125b) as a cantilever and is configured to inwardly deflect toward the longitudinal axis. In addition, each detent arm (128) further includes a detent cam (144), whereas body (18) includes a cam ramp (146) rigidly positioned within mount slots (138) between mount plates (140). During downward translation, cam ramps (146) have an upper ramp surface (148) configured to direct detent cams (144) inwardly, thereby resiliently deflecting detent arms (128) inwardly as shown in FIG. 8B until clearing cam ramps (146) and reaching the engaged position as shown in FIG. 7B and FIG. 8C. As each detent arm (128) resiliently returns outwardly, detent cam (144) of detent arm (128) is thus effectively captured underneath cam ramp (146) for securing catch surface (127) against engagement collar (126) with the predetermined compression force to inhibit rotation of engagement collar (126) up to the predetermined torque.

Furthermore, each detent arm (144) is configured to inwardly deflect again to release detent cam (144) upwardly from underneath cam ramp (146) as the applied torque exceeds the predetermined torque and overcomes the predetermined compression force for allowing engagement collar (126) to slip relative to catch surface (127). In the present example shown in FIGS. 8C-8D, each detent cam (144) includes an upper cam surface (150) engaged with a lower ramp surface (152) of cam ramp (146) securing catch surface (127) against flat (130) of engagement collar (126). Rotating engagement collar (126) with torque approaching the predetermined torque causes engagement collar (126) to urge catch surface (127) upwardly. Detent arms (128) are similarly pulled upwardly, causing detent arms (128) to deflect inwardly as lower ramp surfaces (152) guide upper cam surfaces (150) inwardly until clearing cam ramps (146) as shown in FIG. 8D. Notably, detent cams (144) are configured to clear cam ramps (146) just as the applied torque exceeds the predetermined torque, thereby overcoming the predetermined compression. Engagement collar (126) and transducer assembly (30) may thus slip relative to catch surface (127) to inhibit overtightening waveguide (38) with transducer assembly beyond the predetermined torque.

In the present example, spring (132), detent arms (128), catch surface (127), and engagement collar (126) are collectively tuned to inhibit rotation of transducer assembly (30) up to the predetermined torque to enable tightening of waveguide (38) with transducer assembly (30); yet allow for slippage beyond the predetermined torque to inhibit overtightening of waveguide (38) with transducer assembly (30). In the event that alternative and/or additional mechanisms are incorporated into an alternative slip lock, it will be appreciated that similar tuning may be done in accordance with the invention. The invention is thus not intended to be unnecessarily limited to the particular arrangement of spring (132), detent arms (128), catch surface (127), and engagement collar (126) described herein.

In use, shaft assembly (14) is initially uncoupled from transducer assembly (30). The user translates lock switch (114) of slip lock (110) downwardly from the unlocked position to the locked position such that catch surface (127) of arrester (124) engages engagement collar (126) to seize rotation of transducer assembly (30) relative to body (18). In addition, detent arms (128) of arrester (124) inwardly deflect and are captured underneath cam ramps (146) to releasably secure catch surface (127) against one of flats (130) such that arrester (124) is in the engaged position.

The user then introduces the proximal end portion of waveguide (38) into threaded hole (not shown) of transducer assembly (30) and rotates knob (54) in a tightening direction to threadably engage the proximal end portion of waveguide (38) with transducer assembly (30). Even as frictional engagement between the waveguide (38) and transducer assembly (30) increases, in turn increasing applied torque, catch surface (127) of arrester (124) continues to compress with the predetermined compression against flat (130) to inhibit rotation of engagement collar (126). The user thus continues to tighten waveguide (38) into transducer assembly (30) until reaching the predetermined torque. As applied torque increases, flat (130) of engagement collar (126) urges catch surface (127) upwardly and, in turn, detent arms (128) inwardly deflect until clearing cam ramps (146) and reaching the predetermined torque. Once detent arms (128) are clear of cam ramps (146), catch surface (127) releases flat (130) such that engagement collar (126) and transducer assembly are again free to rotate about the longitudinal axis for inhibiting overtightening of waveguide (38) therein. In the present example, spring (132) then further directs arrester (124) upwardly to the disengaged position with lock switch (114) also returning to the unlocked position.

In some other versions, arrester (124) may remain in the engaged position, yet simply allow slippage of transducer assembly (30) beyond the predetermined torque to inhibit overtightening with waveguide (38). In some such alternatives, the user may then manually manipulate lock switch (114) and arrester (124) to their respective unlocked and disengaged positions as desired. In any case, with waveguide (38) coupled to transducer assembly (30) at the predetermined torque, the user may then collectively rotate waveguide (38) and transducer assembly via knob (54) during the surgical procedure.

By way of further example, slippage of catch surface (127) relative to flats (130) and the resilient return of detent arms (128) inwardly to their original position may also generate an audible indicator, a tactile indicator, or other signal to the user that waveguide (38) is coupled with transducer assembly (30) at the predetermined torque. Slip lock (110) may thus also provide an integral torque indicator for indicating to the user that waveguide (38) has been coupled to the transducer assembly (30) with the predetermined torque.

B. Exemplary Integral Pivot Slip Lock

FIGS. 9A-14C illustrate second exemplary torque wrench (210), such as an integral slip lock (210) of surgical instrument (212), which is configured to both inhibit rotation of transducer assembly (30) and limit torque applied to waveguide (38) to the predetermined torque. As shown in FIGS. 9A-9B, slip lock (210) includes a lock switch (214) pivotally mounted on a laterally extending shaft (215) (see FIG. 11A) such that lock switch (214) extends through a lock channel (216) in body (18). More particularly, lock channel (216) extends longitudinally and transversely through upper surface (118) of body (18) directly above the longitudinal axis. Lock switch (214) is thus pivotable between an unlocked position and a locked position for respectively unlocking and locking rotation of transducer assembly (30) relative to body (18). While lock switch (214) and lock channel (216) are positioned on upper surface (118) of body (18) of the present example, it will be appreciated that lock switch (214) and lock channel (216) may be alternatively positioned to cooperate with transducer assembly (30). The invention is thus not intended to be unnecessarily limited to having lock switch (214) and lock channel (216) positioned as shown herein.

Figure 10B:
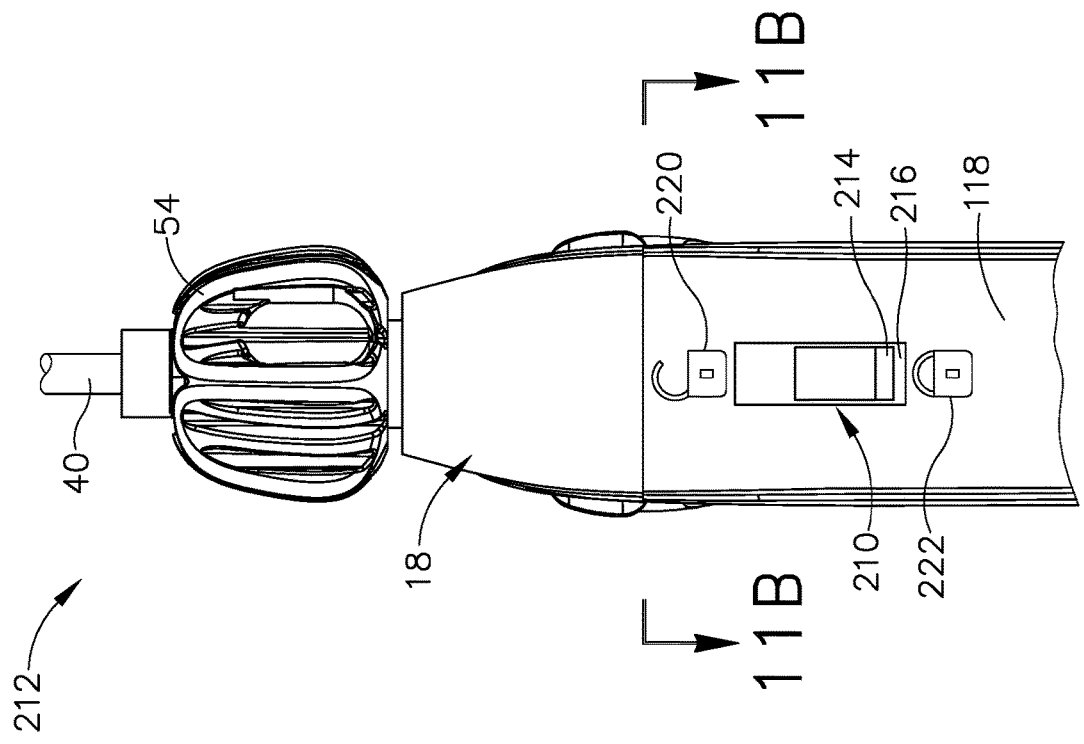
FIG. 10B depicts an enlarged top view of the pivot slip lock of FIG. 9B in the locked position.
Figure 10A:
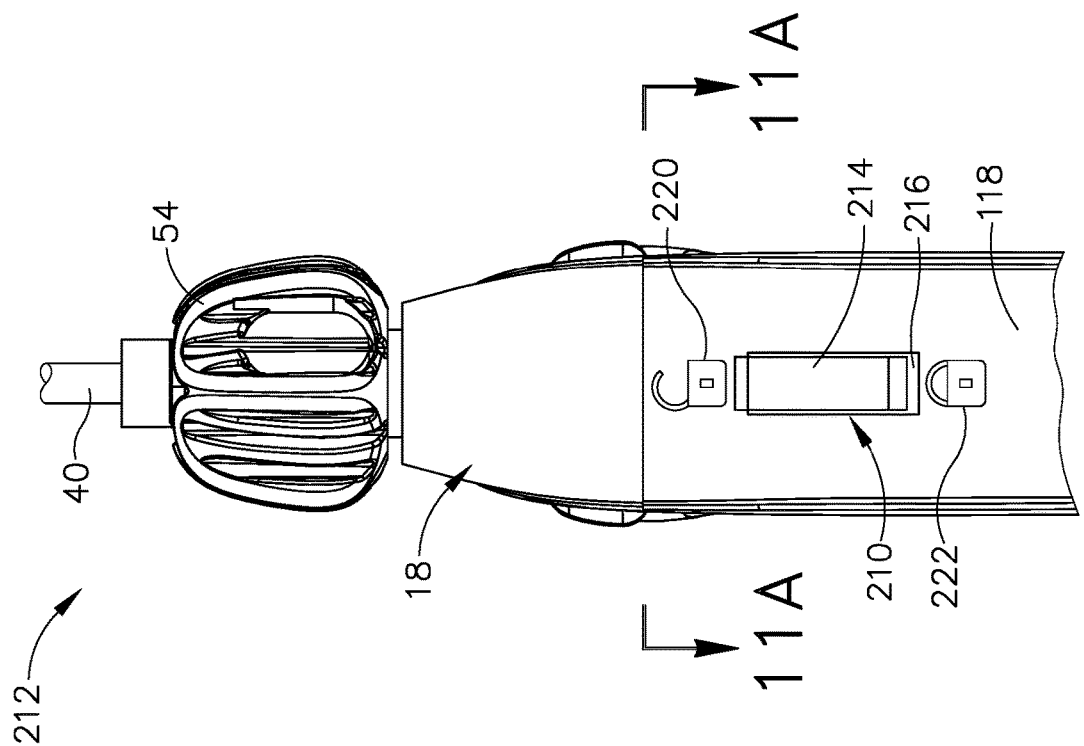
FIG. 10A depicts an enlarged top view of the pivot slip lock of FIG. 9A in the unlocked position.

As seen in FIGS. 10A-10B, upper surface (118) further includes an unlocked indicia (220) and a locked indicia (222) for visually indicating a rotational state (i.e., unlocked state or locked state) of transducer assembly (30) to the user. The present example has unlocked indicia (220) positioned adjacent to a distal end of lock channel (216), whereas locked indicia (222) is positioned adjacent to a proximal end of lock channel (216). Unlocked indicia (220) more particularly includes an image of an unlocked padlock, and locked indicia (222) more particularly includes an image of a locked padlock. However, it will be appreciated that these particular images and positions may vary in accordance with the invention herein and should not be unnecessarily limited to these particular unlocked and locked indicia (220, 222). Furthermore, slip lock (110) may also include one or more cooperating detents (not shown) to releasably secure lock switch (214) in either of the unlocked and locked positions. In some variations, lock switch (214) may be biased toward the unlocked position such that the user would hold lock switch (214) in the locked position while coupling with waveguide (38). The invention is thus not intended to be unnecessarily limited to either secured or biased lock switch (214) positions.

As seen in FIGS. 9A-9B and FIGS. 11A-11B, slip lock (210) further includes an arrester (224) operatively connected to lock switch (214) and an engagement feature (226) operatively connected to transducer assembly (30). Arrester (224) and engagement feature (226) are configured to cooperate with each other to selectively allow or inhibit rotation of transducer assembly (30) relative to body (18). To this end, arrester (224) extends from lock switch (214) within body (18) for transverse engagement with engagement feature (226) and pivots about shaft (215). For example, with lock switch (214) in the unlocked position, arrester (224) faces proximally and is offset from engagement feature (226); but, with lock switch (214) in the locked position, arrester (224) pivots downwardly to transversely engage engagement feature (226). While such pivoting of arrester (224) includes a longitudinal component of movement as well as a transverse component of movement, it will be appreciated that the engagement itself occurs from arrester (224) extending transversely downwardly from lock switch (214). The invention is thus not intended to be limited to only pivoting movement of arrester (224) and/or lock switch (214), and it will be appreciated that such transverse engagement may refer to translation, rotation, or any other movement that includes at least some component of transverse engagement.

Figure 12:
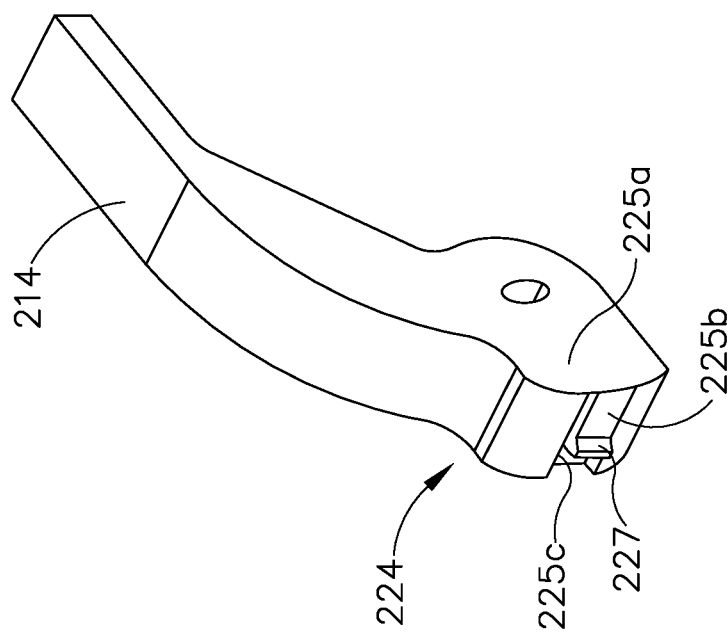
FIG. 12 depicts a perspective view of a lock switch and an arrester of the pivot slip lock of FIG. 9A.

Lock switch (214) and arrester (224) are shown with respect to FIG. 12 in greater detail. In the present example, lock switch (214) and arrester (224) are integrally and unitarily formed together. However, it will be appreciated that lock switch (214) and arrester (224) may alternatively be mechanically coupled relative to each other in accordance with the invention described herein. Furthermore, arrester (224) has a catch portion and a deflectable portion. The deflectable portion of arrester (224) includes an arrester base (225a) extending opposite of lock switch (214) and a lateral catch arm (225b) nested within a lateral groove (225c) of arrester base (225a). Lateral catch arm (225b) is configured to deflect relative to arrester base (225a) and extends laterally as a resilient cantilever from arrester base (225a) to the catch portion, which includes a catch cam (227). Catch cam (227) in conjunction with resilient, lateral catch arm (225b) is configured to deflect relative to engagement feature (227) upon application of torque greater than the predetermined torque at waveguide (38) to release engagement feature (226) for limiting torque to the predetermined torque. In the present example, arrester base and lateral catch arm (225a, 225b) are resiliently connected such that lateral catch arm (225b) deflects upwardly within lateral groove (225c) relative to arrester base (225a), However, it will be appreciated that catch cam (227) may be directed to move via alternative deflection of another portion of slip lock (210). The invention is thus not intended to be unnecessarily limited to the particular deflection between arrester base and lateral catch arm (225a, 225b) described herein.

Figure 13:
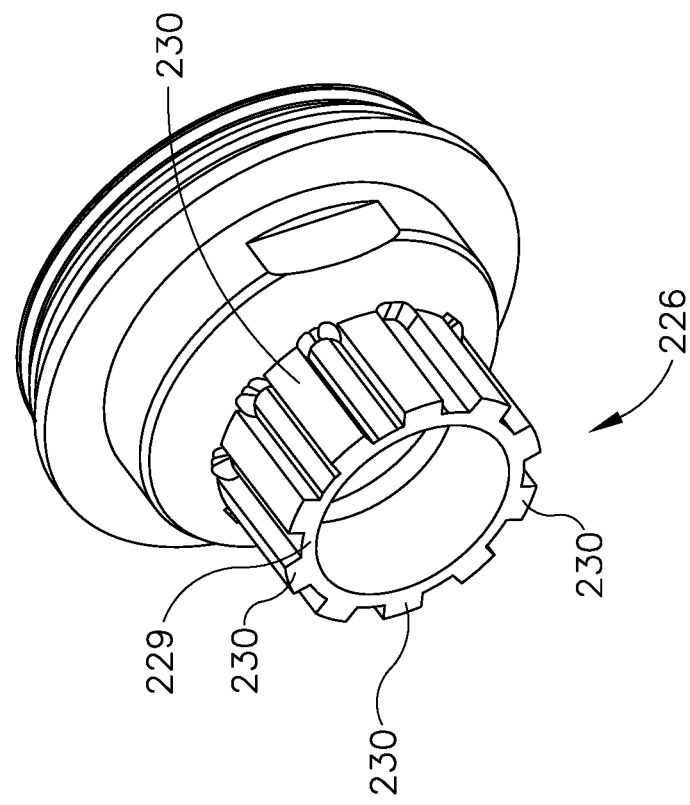
FIG. 13 depicts a perspective view of an engagement collar of the pivot slip lock of FIG. 9A.

Engagement feature (226) of the present example shown in FIG. 13 is more particularly in the form of an engagement collar (226) having an annular collar body (229) and a plurality of teeth (230) positioned angularly about annular collar body (229). Each tooth (230) extends radially outwardly from annular collar body (229) such that any pair of teeth (230) is configured to receive catch cam (227) of arrester (224) therebetween. Furthermore, engagement collar (226) is rigidly secured to a distal end portion of transducer assembly (30) (see FIG. 9A) and positioned concentrically about the longitudinal axis. Engagement collar (226) is thus rotatably fixed relative to transducer assembly (30) such that each may either rotate together relative to body (18) or be rotatably secured together relative to body (18).

Figure 11A:
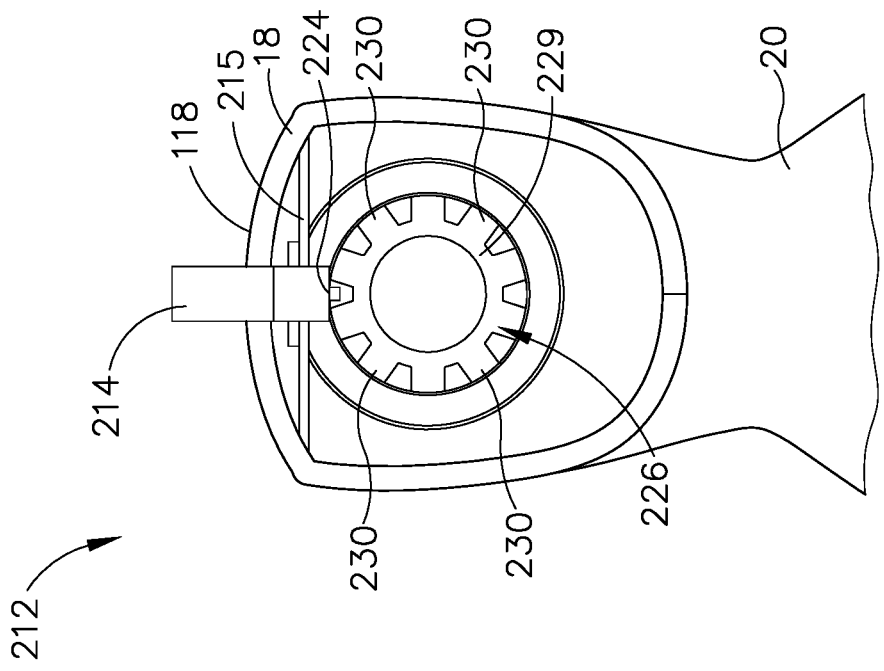
FIG. 11A depicts a cross-sectional view of the ultrasonic surgical instrument of FIG. 10A, taken along section line 11A-11A of FIG. 10A, with the pivot slip lock in the unlocked position.
Figure 11B:
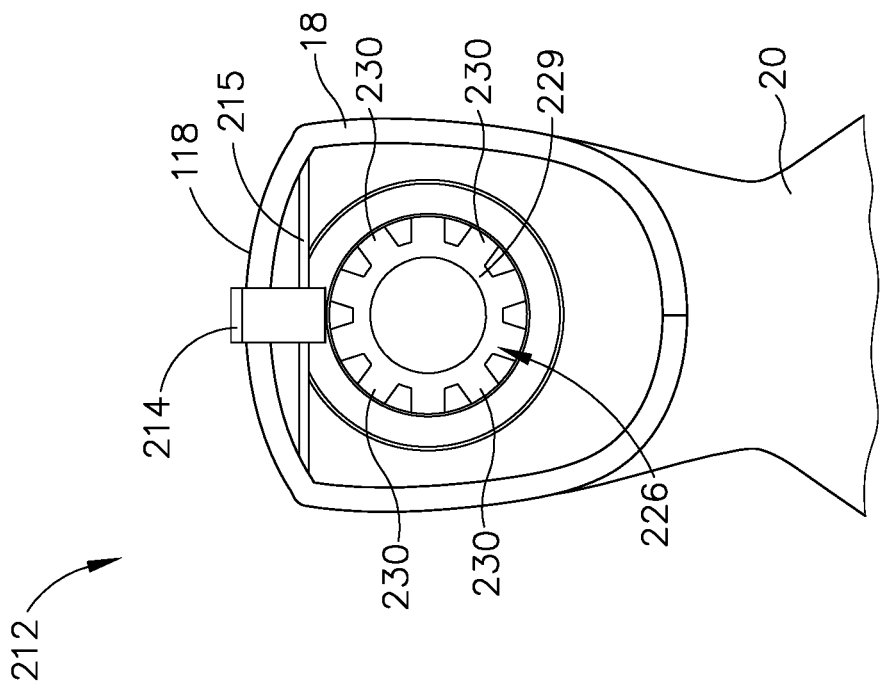
FIG. 11B depicts a cross-sectional view of the ultrasonic surgical instrument of FIG. 10B, taken along section line 11B-11B of FIG. 10B, with the pivot slip lock in the locked position.

FIGS. 9A and 11A illustrate lock switch (214) in the unlocked position with arrester (224) in an upper, disengaged position, offset from engagement collar (226). Upward Proximal rotation of lock switch (214) from the unlocked position toward the locked position pivots arrester (224) downward and distal from the disengaged position toward the engaged position shown in FIGS. 9B and 11B. In the engaged position, catch cam (227) of arrester (224) radially aligns between teeth (230) such that arrester (224) effectively engages teeth (230) to seize rotation of engagement collar (226) relative to body (18). In turn, engagement collar (226) inhibits further rotation of transducer assembly (30) relative to body (18).

In addition, as shown in FIGS. 14A-14C, catch cam (227) has a driven cam surface (232), while each tooth (230) has a drive cam surface (234). Driven and drive cam surfaces (232, 234) cooperate such that drive cam surface (234) rotates against driven cam surface (234) to seize engagement collar (226) with arrester (224) as shown in FIG. 14B.

However, as the applied torque increases while coupling waveguide (38) (see FIG. 9A) with transducer assembly (30) (see FIG. 9A) toward the predetermined torque, drive cam surface (234) of engagement collar (226) directs driven cam surface (232) upwardly, eventually providing deflection of lateral catch arm (225b) relative to arrester base (225a). So long as drive and driven cam surfaces (234, 232) remain engaged with catch cam (227) between teeth (230), engagement collar (226) remains seized relative to arrester (224) and body (18) for tightening waveguide (38) (see FIG. 9B). Once the applied torque increases beyond the predetermined torque as shown in FIG. 14C, the relative deflection of lateral catch arm (225b) with catch cam (227) is configured to lift catch cam (227) from engagement collar (226) such that catch cam rotatably releases engagement collar (226). In turn, engagement collar (226) rotatably slips relative to catch cam (227) to inhibit overtightening of waveguide (38) (see FIG. 9B) with transducer assembly (30) (see FIG. 9B) beyond the predetermined torque. In other words, the deflection of lateral catch arm (225b) with catch cam (227) is collectively tuned to the predetermined torque to both inhibit rotation of transducer assembly (30) (see FIG. 9B) up to the predetermined torque as well as release engagement collar (226) beyond the predetermined torque for relative slippage of transducer assembly (30) (see FIG. 9B).

In use, shaft assembly (14) is initially uncoupled from transducer assembly (30). The user pivots lock switch (214) of slip lock (210) from the unlocked position to the locked position such that catch cam (227) of arrester (224) engages engagement collar (226) to seize rotation of transducer assembly (30) relative to body (18). The user then introduces the proximal end portion of waveguide (38) into threaded hole (not shown) of transducer assembly (30) and rotates knob (54) in a tightening direction to threadably engage the proximal end portion of waveguide (38) with transducer assembly (30). Even as frictional engagement between the waveguide (38) and transducer assembly (30) increases, in turn increasing applied torque, arrester (224) continues to block rotation of teeth (230) on engagement collar (226). The user thus continues to tighten waveguide (38) into transducer assembly (30) until reaching the predetermined torque. As applied torque increases, catch cam (227) deflects upwardly until reaching the predetermined torque and, in turn, releases engagement collar (226) for relative slippage to inhibit overtightening of waveguide (38). Catch cam (227) of the present example resiliently returns downwardly between another pair of teeth (230) and, in the event that torque continues to be applied, catch cam (227) will continue to deflect and slip to inhibit overtightening of waveguide (38). The user then pivots lock switch (214) back to the unlocked position to withdraw arrester (224) from engagement collar (226) such that waveguide (38) and transducer assembly (30) may be collectively rotated unitarily via knob (54) during the surgical procedure.

By way of further example, slippage of catch cam relative to teeth (230) and the resilient return of catch cam (227) downwardly to its original position may also generate an audible indicator, a tactile indicator, or other signal to the user that waveguide (38) is coupled with transducer assembly (30) at the predetermined torque. Slip lock (210) may thus also provide an integral torque indicator for indicating to the user that waveguide (38) has been coupled to the transducer assembly (30) with the predetermined torque.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) an instrument body; (b) an ultrasonic transducer assembly rotatably mounted along a longitudinal axis within the instrument body; and (c) a slip lock operatively connected to the instrument body and including: (i) a lock member configured to be selectively moved between an unlocked position and a locked position, and (ii) an arrester having a catch portion and a deflectable portion, wherein the deflectable portion is configured to deflect relative to the ultrasonic transducer assembly, wherein the ultrasonic transducer assembly is configured to be selectively rotated about the longitudinal axis relative to the instrument body with the lock member in the unlocked position, wherein the catch portion is configured to seize the ultrasonic transducer assembly with the lock member in the locked position to thereby selectively inhibit rotation about the longitudinal axis relative to the instrument body for rotatably coupling with the acoustic waveguide up to a predetermined torque, and wherein the deflectable portion is configured to deflect relative to the ultrasonic transducer assembly upon receiving a torque greater than the predetermined torque such that the catch portion releases the ultrasonic transducer assembly to slip relative to the catch portion for limiting coupling of the ultrasonic transducer assembly with the acoustic waveguide to the predetermined torque.

EXAMPLE 2

The surgical instrument of Example 1, wherein the instrument body includes a switch channel, wherein the lock member includes a lock switch movably mounted in the switch channel, and wherein the lock switch is configured to be manipulated by a user between the locked and unlocked positions.

EXAMPLE 3

The surgical instrument of Example 2, wherein the slip lock further includes an engagement feature connected to the ultrasonic transducer assembly, wherein the arrester is operatively connected to the lock switch and is configured to selectively move between a disengaged position and an engaged position as the lock switch is respectively moved between the unlocked position and the locked position, and wherein the catch portion of the arrester is configured to engage the engagement feature in the engaged position to inhibit rotation of the ultrasonic transducer assembly.

EXAMPLE 4

The surgical instrument of Example 3, wherein the lock switch is configured to selectively translate along a transverse direction between the unlocked and the locked position to selectively translate the arrester transversely between the disengaged position and the engaged position.

EXAMPLE 5

The surgical instrument of any one or more of Examples 3 through 4, wherein the lock switch is configured to selectively pivot along a transverse direction between the unlocked position and the locked position to selectively pivot the arrester transversely between the disengaged position and the engaged position.

EXAMPLE 6

The surgical instrument of any one or more of Examples 3 through 5, wherein the engagement feature includes an engagement collar connected to the ultrasonic transducer assembly and positioned concentrically about the longitudinal axis, and wherein the catch portion of the arrester is configured to be received against the engagement collar in the engaged position thereby inhibiting rotation of the engagement collar and the ultrasonic transducer assembly connected thereto up to the predetermined torque.

EXAMPLE 7

The surgical instrument of Example 6, wherein the engagement collar has at least one flat extending therealong, and the lock switch and arrester are configured to be selectively moved toward the longitudinal axis such that the catch portion of the arrester engages the at least one flat to thereby inhibit rotation of the ultrasonic transducer assembly connected thereto up to the predetermined torque.

EXAMPLE 8

The surgical instrument of Example 7, wherein the deflectable portion of the arrester is configured to releasably engage a portion of the instrument body in the engaged position and thereby releasably secure the catch portion of the arrester against the at least one flat for inhibiting rotation of the ultrasonic transducer assembly, and wherein the engagement collar with torque applied greater than the predetermined torque is configured to direct the catch portion from the engaged position toward the disengaged position and thereby deflect the deflectable portion of the arrester to release the portion of the instrument body such that the engagement collar and ultrasonic transducer assembly slip relative to the catch portion.

EXAMPLE 9

The surgical instrument of any one or more of Examples 6 through 8, wherein the engagement collar has a plurality of teeth positioned angularly about the engagement collar, and wherein the catch portion of the arrester is configured to be received between the plurality of teeth in the engaged position thereby inhibiting rotation of the engagement collar and the ultrasonic transducer assembly connected thereto up to the predetermined torque.

EXAMPLE 10

The surgical instrument of Example 9, wherein the catch portion of the arrester extends from the deflectable portion of the arrester to the plurality of teeth of the engagement collar in the engaged position to thereby releasably secure the catch portion of the arrester between the plurality of teeth for inhibiting rotation of the ultrasonic transducer assembly, and wherein the engagement collar with torque applied greater than the predetermined torque is configured to thereby deflect the deflectable portion of the arrester to release the plurality of teeth such that the engagement collar and the ultrasonic transducer assembly slip relative to the catch portion.

EXAMPLE 11

The surgical instrument of any one or more of Examples 1 through 10, wherein the deflectable portion of the arrester is configured to deflect relative to the catch portion of the arrester.

EXAMPLE 12

The surgical instrument of Example 11, wherein the deflectable portion of the arrester includes a resilient detent arm, wherein the detent arm is configured to releasably engage a portion of the instrument body with the lock member in the locked position thereby seizing the ultrasonic transducer assembly with the catch portion of the arrester up to the predetermined torque, wherein the resilient detent arm is configured to deflect upon application of torque greater than the predetermined torque on the ultrasonic transducer assembly such that the detent arm releases the portion of the instrument body and the ultrasonic transducer assembly slips relative to the catch portion.

EXAMPLE 13

The surgical instrument of any one or more of Examples 1 through 12, wherein the catch portion and the deflectable portion are configured to collectively deflect together relative to the ultrasonic transducer assembly.

EXAMPLE 14

The surgical instrument of Example 13, wherein the deflectable portion of the arrester includes a resilient catch arm, wherein the catch portion of the arrester extends from the resilient catch arm toward the ultrasonic transducer assembly, wherein the catch portion of the arrester is configured to seize the ultrasonic transducer assembly with the lock member in the locked position up to the predetermined torque, wherein the resilient catch arm and the catch portion of the arrester are configured to collectively deflect upon application of torque greater than the predetermined torque on the ultrasonic transducer assembly such that the ultrasonic transducer assembly slips relative to the catch portion.

EXAMPLE 15

The surgical instrument of any one or more of Examples 1 through 14, further comprising a shaft assembly having an acoustic waveguide extending therethrough, wherein the end effector projects distally from the shaft assembly, and wherein the acoustic waveguide has a proximal end portion configured to rotatably couple with the ultrasonic transducer assembly.

EXAMPLE 16

A surgical instrument, comprising: (a) an instrument body; (b) an ultrasonic transducer assembly rotatably mounted along a longitudinal axis within the instrument body; and (c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes: (i) an engagement feature secured to the ultrasonic transducer assembly such that the engagement feature is configured to rotate with the ultrasonic transducer feature, (ii) a catch surface configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque, and (iii) a resiliently deflectable detent arm configured to releasably engage a portion of instrument body with the slip lock in the engaged position to releasably secure the catch surface in the engaged position, wherein the engagement feature is configured to urge the catch surface toward the disengaged position upon the ultrasonic transducer assembly receiving a torque greater than the predetermined torque such that the detent arm resiliently deflects to release the portion of the instrument body and the ultrasonic transducer assembly slips relative to the catch surface for limiting coupling of the ultrasonic transducer assembly with the acoustic waveguide to the predetermined torque.

EXAMPLE 17

The surgical instrument of Example 16, wherein the engagement feature includes an engagement collar connected to the ultrasonic transducer assembly and positioned concentrically about the longitudinal axis, and wherein the catch surface is configured to be received against the engagement collar in the engaged position thereby inhibiting rotation of the engagement collar and the ultrasonic transducer assembly connected thereto up to the predetermined torque.

EXAMPLE 18

The surgical instrument of Example 17, wherein the engagement collar has at least one flat extending therealong, wherein the catch surface is configured to be selectively moved toward the longitudinal axis such that the catch surface engages the at least one flat to thereby inhibit rotation of the ultrasonic transducer assembly connected thereto up to the predetermined torque.

EXAMPLE 19

A surgical instrument, comprising: (a) an instrument body; (b) an ultrasonic transducer assembly rotatably mounted along a longitudinal axis within the instrument body; and (c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes: (i) an engagement feature secured to the ultrasonic transducer assembly such that the engagement feature is configured to rotate with the ultrasonic transducer feature, (ii) a catch arm configured to resiliently deflect, and (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque, wherein the engagement feature is configured to urge the catch cam therewith upon the ultrasonic transducer assembly receiving a torque greater than the predetermined torque such that the catch arm resiliently deflects with the catch cam until the catch cam releases the engagement feature and the ultrasonic transducer assembly slips relative to the catch cam for limiting coupling of the ultrasonic transducer assembly with the acoustic waveguide to the predetermined torque.

EXAMPLE 20

The surgical instrument of Example 19, wherein the engagement feature includes an engagement collar connected to the ultrasonic transducer assembly and positioned concentrically about the longitudinal axis, and wherein the catch cam is configured to be received against the engagement collar in the engaged position thereby inhibiting rotation of the engagement collar and the ultrasonic transducer assembly connected thereto up to the predetermined torque.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument, comprising:
   (a) an instrument body, wherein the instrument body includes a switch channel;
   (b) an ultrasonic transducer assembly rotatably mounted along a longitudinal axis within the instrument body; and
   (c) a slip lock operatively connected to the instrument body and including:
      (i) a lock member configured to be selectively moved between an unlocked position and a locked position, wherein the lock member includes a lock switch movably mounted in the switch channel,
      (ii) an arrester having a catch portion and a deflectable portion, wherein the deflectable portion is configured to deflect relative to the ultrasonic transducer assembly, and
      (iii) an engagement feature connected to the ultrasonic transducer assembly,
   wherein the ultrasonic transducer assembly is configured to be selectively rotated about the longitudinal axis relative to the instrument body with the lock member in the unlocked position,
   wherein the arrester is operatively connected to the lock switch and is configured to selectively move between a disengaged position and an engaged position as the lock switch is respectively moved between the unlocked position and the locked position,
   wherein the catch portion is configured to seize the ultrasonic transducer assembly with the lock member in the locked position to thereby selectively inhibit rotation about the longitudinal axis relative to the instrument body for rotatably coupling with the acoustic waveguide up to a predetermined torque, wherein the catch portion of the arrester is configured to engage the engagement feature in the engaged position to inhibit rotation of the ultrasonic transducer assembly,
   wherein the lock switch is configured to selectively move along a transverse direction relative to the longitudinal axis between the unlocked and the locked position to selectively translate the arrester transversely between the disengaged position and the engaged position, and
   wherein the deflectable portion is configured to deflect relative to the ultrasonic transducer assembly upon receiving a torque greater than the predetermined torque such that the catch portion releases the ultrasonic transducer assembly to slip relative to the catch portion for limiting coupling of the ultrasonic transducer assembly with the acoustic waveguide to the predetermined torque.

2. The surgical instrument of claim 1, wherein the lock switch is configured to be manipulated by a user between the locked and unlocked positions.

3. The surgical instrument of claim 1, wherein the lock switch is configured to selectively translate along a transverse direction between the unlocked and the locked position to selectively translate the arrester transversely between the disengaged position and the engaged position.

4. The surgical instrument of claim 1, wherein the lock switch is configured to selectively pivot along a transverse direction between the unlocked position and the locked position to selectively pivot the arrester transversely between the disengaged position and the engaged position.

5. The surgical instrument of claim 1, wherein the engagement feature includes an engagement collar connected to the ultrasonic transducer assembly and positioned concentrically about the longitudinal axis, and wherein the catch portion of the arrester is configured to be received against the engagement collar in the engaged position thereby inhibiting rotation of the engagement collar and the ultrasonic transducer assembly connected thereto up to the predetermined torque.

6. The surgical instrument of claim 5, wherein the engagement collar has at least one flat extending therealong, and the lock switch and arrester are configured to be selectively moved toward the longitudinal axis such that the catch portion of the arrester engages the at least one flat to thereby inhibit rotation of the ultrasonic transducer assembly connected thereto up to the predetermined torque.

7. The surgical instrument of claim 6, wherein the deflectable portion of the arrester is configured to releasably engage a portion of the instrument body in the engaged position and thereby releasably secure the catch portion of the arrester against the at least one flat for inhibiting rotation of the ultrasonic transducer assembly, and wherein the engagement collar with torque applied greater than the predetermined torque is configured to direct the catch portion from the engaged position toward the disengaged position and thereby deflect the deflectable portion of the arrester to release the portion of the instrument body such that the engagement collar and ultrasonic transducer assembly slip relative to the catch portion.

8. The surgical instrument of claim 5, wherein the engagement collar has a plurality of teeth positioned angularly about the engagement collar, and wherein the catch portion of the arrester is configured to be received between the plurality of teeth in the engaged position thereby inhibiting rotation of the engagement collar and the ultrasonic transducer assembly connected thereto up to the predetermined torque.

9. The surgical instrument of claim 8, wherein the catch portion of the arrester extends from the deflectable portion of the arrester to the plurality of teeth of the engagement collar in the engaged position to thereby releasably secure the catch portion of the arrester between the plurality of teeth for inhibiting rotation of the ultrasonic transducer assembly, and wherein the engagement collar with torque applied greater than the predetermined torque is configured to thereby deflect the deflectable portion of the arrester to release the plurality of teeth such that the engagement collar and the ultrasonic transducer assembly slip relative to the catch portion.

10. The surgical instrument of claim 1, wherein the deflectable portion of the arrester is configured to deflect relative to the catch portion of the arrester.

11. The surgical instrument of claim 10, wherein the deflectable portion of the arrester includes a resilient detent arm, wherein the detent arm is configured to releasably engage a portion of the instrument body with the lock member in the locked position thereby seizing the ultrasonic transducer assembly with the catch portion of the arrester up to the predetermined torque, wherein the resilient detent arm is configured to deflect upon application of torque greater than the predetermined torque on the ultrasonic transducer assembly such that the detent arm releases the portion of the instrument body and the ultrasonic transducer assembly slips relative to the catch portion.

12. The surgical instrument of claim 1, wherein the catch portion and the deflectable portion are configured to collectively deflect together relative to the ultrasonic transducer assembly.

13. The surgical instrument of claim 12, wherein the deflectable portion of the arrester includes a resilient catch arm, wherein the catch portion of the arrester extends from the resilient catch arm toward the ultrasonic transducer assembly, wherein the catch portion of the arrester is configured to seize the ultrasonic transducer assembly with the lock member in the locked position up to the predetermined torque, wherein the resilient catch arm and the catch portion of the arrester are configured to collectively deflect upon application of torque greater than the predetermined torque on the ultrasonic transducer assembly such that the ultrasonic transducer assembly slips relative to the catch portion.

14. The surgical instrument of claim 1, further comprising a shaft assembly having an acoustic waveguide extending therethrough, wherein the end effector projects distally from the shaft assembly, and wherein the acoustic waveguide has a proximal end portion configured to rotatably couple with the ultrasonic transducer assembly.

15. The surgical instrument of claim 1, wherein the arrester is resiliently biased toward the disengaged position.

16. A surgical instrument, comprising:
(a) an instrument body, wherein the instrument body includes a switch channel;
(b) an ultrasonic transducer assembly rotatably mounted along a longitudinal axis within the instrument body; and
(c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes:
  (i) an engagement feature secured to the ultrasonic transducer assembly such that the engagement feature is configured to rotate with the ultrasonic transducer feature,
  (ii) a catch surface configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque,
  (iii) a resiliently deflectable detent arm configured to releasably engage a portion of instrument body with the slip lock in the engaged position to releasably secure the catch surface in the engaged position, and
  (iv) a lock switch movably mounted in the switch channel, wherein the lock switch is configured to selectively translate along a transverse direction relative to the longitudinal axis between an unlocked and a locked position to selectively translate the catch portion transversely between the disengaged position and the engaged position,
wherein the engagement feature is configured to urge the catch surface toward the disengaged position upon the ultrasonic transducer assembly receiving a torque greater than the predetermined torque such that the detent arm resiliently deflects to release the portion of the instrument body and the ultrasonic transducer assembly slips relative to the catch surface for limiting coupling of the ultrasonic transducer assembly with the acoustic waveguide to the predetermined torque.

17. The surgical instrument of claim 16, wherein the engagement feature includes an engagement collar connected to the ultrasonic transducer assembly and positioned concentrically about the longitudinal axis, and wherein the catch surface is configured to be received against the engagement collar in the engaged position thereby inhibiting rotation of the engagement collar and the ultrasonic transducer assembly connected thereto up to the predetermined torque.

18. The surgical instrument of claim 17, wherein the engagement collar has at least one flat extending therealong, wherein the catch surface is configured to be selectively moved toward the longitudinal axis such that the catch surface engages the at least one flat to thereby inhibit rotation of the ultrasonic transducer assembly connected thereto up to the predetermined torque.

19. A surgical instrument, comprising:
   (a) an instrument body, wherein the instrument body includes a switch channel;
   (b) an ultrasonic transducer assembly rotatably mounted along a longitudinal axis within the instrument body; and
   (c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes:
      (i) an engagement feature secured to the ultrasonic transducer assembly such that the engagement feature is configured to rotate with the ultrasonic transducer feature,
      (ii) a catch arm configured to resiliently deflect,
      (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque, and
      (iv) a lock switch movably mounted in the switch channel, wherein the lock switch is configured to selectively pivot along a transverse direction relative to the longitudinal axis between an unlocked position and a locked position to selectively pivot the catch cam transversely between the disengaged position and the engaged position,
   wherein the engagement feature is configured to urge the catch cam therewith upon the ultrasonic transducer assembly receiving a torque greater than the predetermined torque such that the catch arm resiliently deflects with the catch cam until the catch cam releases the engagement feature and the ultrasonic transducer assembly slips relative to the catch cam for limiting coupling of the ultrasonic transducer assembly with the acoustic waveguide to the predetermined torque.

20. The surgical instrument of claim 19, wherein the engagement feature includes an engagement collar connected to the ultrasonic transducer assembly and positioned concentrically about the longitudinal axis, and wherein the catch cam is configured to be received against the engagement collar in the engaged position thereby inhibiting rotation of the engagement collar and the ultrasonic transducer assembly connected thereto up to the predetermined torque.

\* \* \* \* \*